United States Patent
Zhang et al.

(10) Patent No.: US 10,575,837 B2
(45) Date of Patent: Mar. 3, 2020

(54) TISSUE AND VASCULAR CLOSURE DEVICES AND METHODS OF USE THEREOF

(71) Applicant: CardioVantage Medical, Inc., San Mateo, CA (US)

(72) Inventors: Ji Zhang, Burnaby (CA); Brandon G. Walsh, Syracuse, UT (US)

(73) Assignee: Suzhou Jiecheng Medical Technology Co., LTD., Jiangsu (CN)

( * ) Notice: Subject to any disclaimer, the term of this patent is extended or adjusted under 35 U.S.C. 154(b) by 425 days.

(21) Appl. No.: 14/774,016

(22) PCT Filed: Mar. 12, 2014

(86) PCT No.: PCT/US2014/025003
§ 371 (c)(1),
(2) Date: Sep. 9, 2015

(87) PCT Pub. No.: WO2014/159754
PCT Pub. Date: Oct. 2, 2014

(65) Prior Publication Data
US 2016/0022252 A1   Jan. 28, 2016

Related U.S. Application Data

(60) Provisional application No. 61/785,970, filed on Mar. 14, 2013.

(51) Int. Cl.
*A61B 17/04* (2006.01)
*A61B 17/00* (2006.01)
(Continued)

(52) U.S. Cl.
CPC ...... *A61B 17/0057* (2013.01); *A61B 17/0401* (2013.01); *A61B 17/06066* (2013.01);
(Continued)

(58) Field of Classification Search
CPC ............ A61B 17/0057; A61B 17/0401; A61B 2017/00557; A61B 2017/00579;
(Continued)

(56) References Cited

U.S. PATENT DOCUMENTS 7,351,250 B2    4/2008  Zamierowski
2004/0087968 A1*  5/2004  Core ................. A61B 17/3439
                                                  606/108

(Continued)

FOREIGN PATENT DOCUMENTS

JP   2005-511130 A    4/2005
JP   2007-523686      8/2007
(Continued)

OTHER PUBLICATIONS

Partial supplementary European search report dated Oct. 31, 2016, which issued in European Application No. 14773216.8.
(Continued)

*Primary Examiner* — George J Ulsh
(74) *Attorney, Agent, or Firm* — Nathan S. Smith; Sujohn Das; Morgan, Lewis & Bockius LLP

(57) ABSTRACT

Devices and methods for closing access points in tissue are described. The devices include a tubular element fabricated form, for example, biologic material, a biologic tubular structure, or synthetic material. Using minimally invasive procedures, the devices and methods described herein allow implantation of the tubular element through the access point or wound such that it traverses the tissue. The tube has a sealed end which prevents leakage of fluid from, for example, the heart or a vessel upon securing the tube to the tissue.

22 Claims, 25 Drawing Sheets

(51) Int. Cl.
*A61B 17/06* (2006.01)
*A61B 17/064* (2006.01)

(52) U.S. Cl.
CPC .......... *A61B 2017/0065* (2013.01); *A61B 2017/00579* (2013.01); *A61B 2017/00597* (2013.01); *A61B 2017/00623* (2013.01); *A61B 2017/00668* (2013.01); *A61B 2017/047* (2013.01); *A61B 2017/0409* (2013.01); *A61B 2017/0464* (2013.01); *A61B 2017/0472* (2013.01); *A61B 2017/061* (2013.01); *A61B 2017/0649* (2013.01); *A61B 2017/06076* (2013.01)

(58) Field of Classification Search
CPC .......... A61B 2017/00623; A61B 2017/00654; A61B 2017/00659; A61B 2017/00668; A61B 2017/00884; A61B 2017/00951; A61B 2017/00986; A61B 2017/0409; A61B 2017/0464; A61B 2017/047; A61B 2017/0472; A61B 2017/0649; A61B 2017/308; A61B 2017/3484; A61B 2017/06066; A61B 2017/0065; A61B 2017/06076; A61B 2017/061
See application file for complete search history.

(56) References Cited

U.S. PATENT DOCUMENTS

| | | |
|---|---|---|
| 2008/0249562 A1 | 10/2008 | Cahill |
| 2011/0106148 A1 | 5/2011 | Ginn et al. |
| 2011/0172584 A1 | 7/2011 | Chin |
| 2012/0010634 A1 | 1/2012 | Crabb et al. |
| 2012/0089171 A1 | 4/2012 | Hastings et al. |
| 2012/0296372 A1 | 11/2012 | Ziobro |

FOREIGN PATENT DOCUMENTS

| | | | |
|---|---|---|---|
| WO | WO-2004/105621 A1 | 12/2004 | |
| WO | WO-2007/059243 A1 | 5/2007 | |
| WO | WO 2010/085449 A1 | 7/2010 | |
| WO | WO 2010085449 A1 * | 7/2010 | ......... A61B 17/0057 |
| WO | WO 2014/159754 A2 | 10/2014 | |

OTHER PUBLICATIONS

International Search Report from PCT Patent Application No. PCT/US2014/025003 dated Oct. 24, 2014, application now published as International Publication No. WO2014/159754 dated Oct. 2, 2014.

Japanese Office Action from Japanese Patent Application No. 2016-501716, dated Oct. 24, 2017, 6 pages.

* cited by examiner

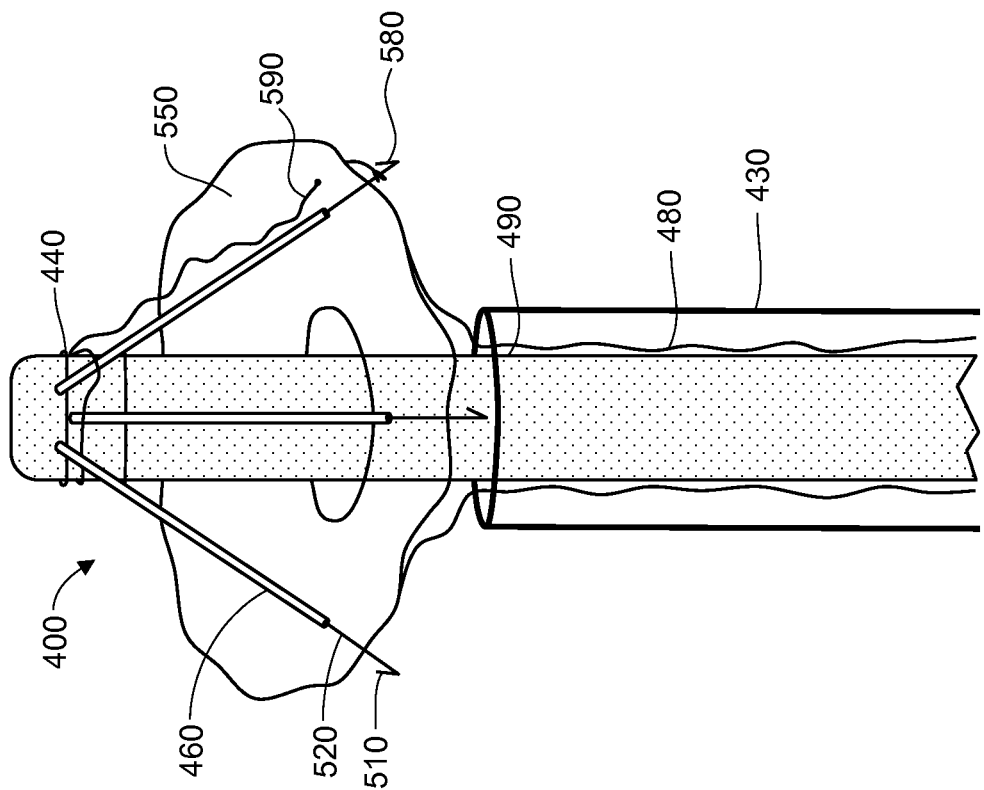
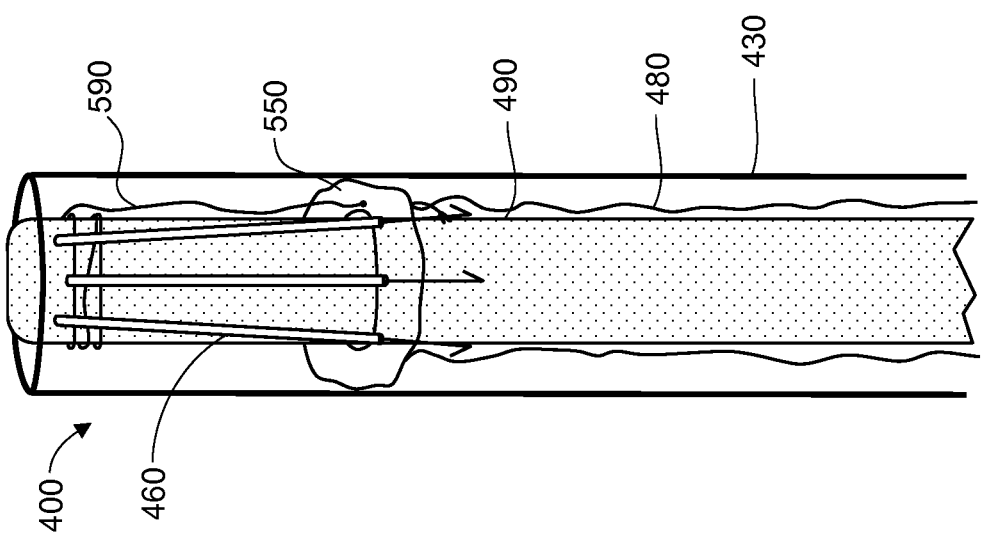

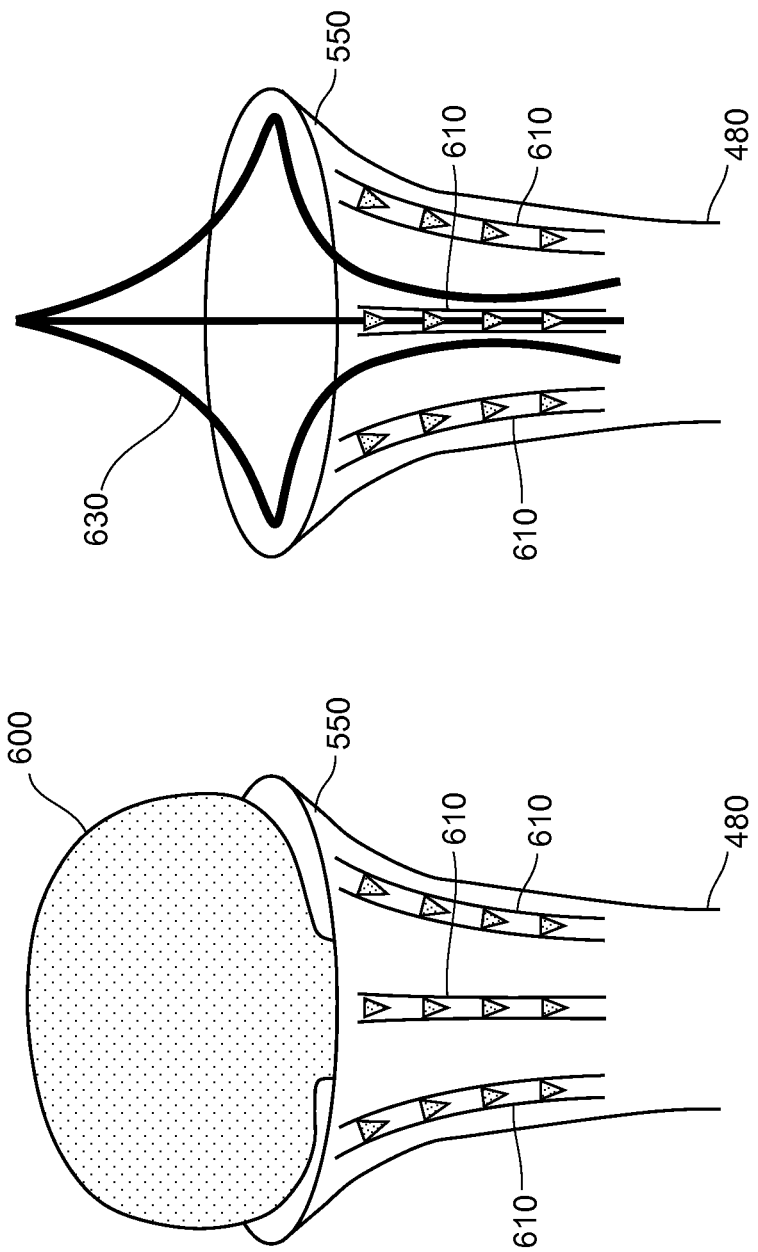

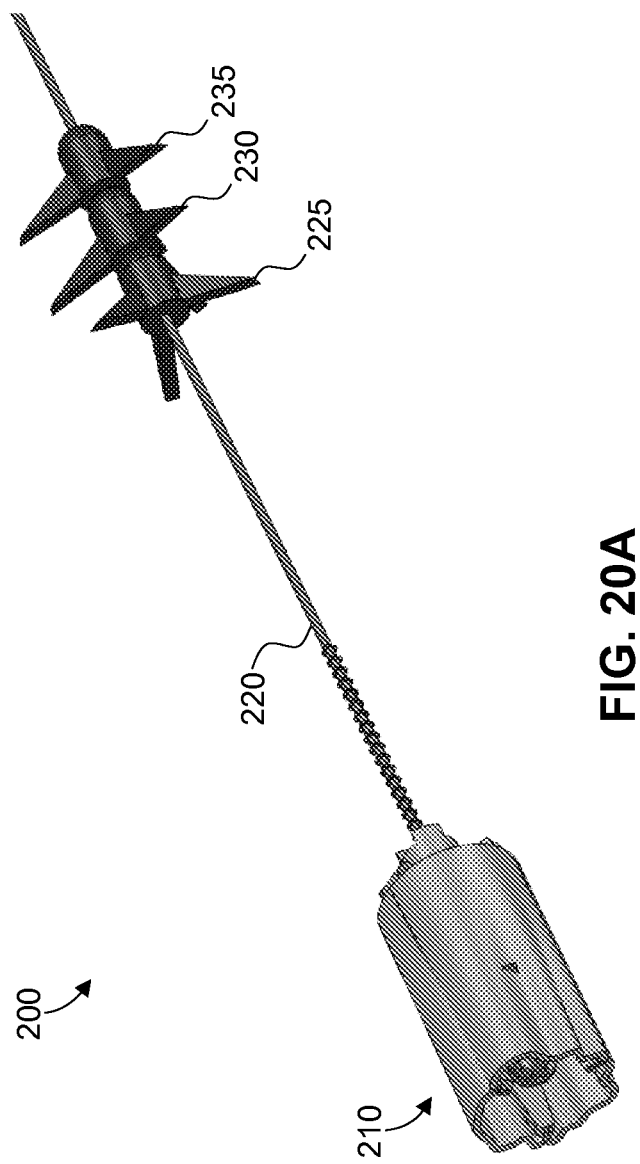

TISSUE AND VASCULAR CLOSURE DEVICES AND METHODS OF USE THEREOF

CROSS REFERENCE TO RELATED APPLICATIONS

This application is a U.S. National Stage of International Patent Application No. PCT/US2014/025003, filed Mar. 12, 2014, which claims the benefit of priority to U.S. Provisional Application No. 61/785,970, filed Mar. 14, 2013, the disclosures of which are all incorporated herein by reference in their entirety.

TECHNICAL FIELD

The subject matter described herein relates to medical devices and methods for the closure of tissue openings generated during minimally invasive surgical techniques.

BACKGROUND

Minimally invasive surgical techniques have emerged as an important trend within the field of surgery. Minimally invasive surgery differs from standard open surgery in that surgical procedures are performed through small incisions in the body under the guidance of endoscopy, fluoroscopy, ultrasound or other remote imaging techniques. Minimally invasive surgical techniques reduce the morbidity of surgical procedures, accelerate patient recovery and, in many cases, also reduce the overall cost of surgery, especially by shortening the recovery period during which patients must stay in the hospital. Examples of minimally invasive surgery include laparoscopic, endoscopic and orthoscopic surgeries.

In recent years, there has been significant advancement of minimally invasive surgical techniques in the area of cardiac surgery. Certain cardiac surgery procedures that previously were only possible through open chest surgery have already been converted to minimally invasive surgical techniques. For example, catheter techniques have been developed for occlusion of patent material septal defects and for valvuloplasty of stenotic aortic or mitral valves. Instruments and techniques have also been developed for endoscopic approaches to the heart, allowing more complex cardiac surgical procedures, for example, the replacement of a stenotic or insufficient mitral valve, to be performed through minimally invasive surgical techniques.

A trocar or introducer is inserted through the incision and medical instruments are introduced into the abdominal cavity therethrough. The surgeon performs procedures inside the cavity by manipulating the medical instruments from outside the patient while viewing the manipulations using a closed circuit monitor connected to an imaging device called a laparoscope that is inserted into the cavity. By using such equipment and procedures, laparoscopic surgery generally results in less trauma to the patient and, consequently, a more rapid recovery than with conventional open surgery. Similar advantages apply to other forms of minimally invasive surgery.

One of the great challenges facing minimally invasive surgery is safe management of access sites after removal of the surgical instrument. In the case of percutaneous catheters, manual compression of the site is the traditional method for closure of the femoral artery, but is associated with a complication rate of up to 5%, marked discomfort and immobility for patients, and prolonged hospitalization. However, new vascular closure devices (VCDs) have been approved by the FDA and have replaced manual compression. These VCDs are associated with decreased length of stay and increased comfort for the patient.

There remains a needed for closure devices which may be used with minimally invasive surgical procedures but which are also simple, reliable and economically feasible.

BRIEF SUMMARY

In one aspect, a tubular closure device is provided.

In one embodiment, the closure device comprises a sealing tube, a plurality of anchors, a pusher cable, and a suture.

In one embodiment, the tube is closed at the first terminus. In another embodiment, the tube is closed at the first terminus by a knot at the first terminus. In still another embodiment, the tube is closed at the first terminus by clipping, pinching, twisting, widging, gluing, or other means with tensor force, chemical bonding, or physical pressure force. In another embodiment, the tube is open at a second terminus. In yet another embodiment, the second terminus comprises a sealing tube end portion.

In one embodiment, the pusher cable is encased at least partially by the sealing tube. In another embodiment, the distal end of the pusher cable comprises a nose cone.

In one embodiment, each of the plurality of anchors comprises a first end and a second end. In another embodiment, each of the plurality of anchors is attached to the nose cone at the first end.

In one embodiment, each of the plurality of anchors is a hollow tube. In another embodiment, each of the plurality of anchors encases a portion of a stake. In yet another embodiment, the stake comprises at least one barb.

In one embodiment, the tubular closure device comprises a suture. In another embodiment, the suture is threaded through at least a portion of the sealing tube. In yet another embodiment, one end of the suture is fastened to the distal end of the pusher cable. In still another embodiment, one end of the suture is fastened to the nose cone.

In one embodiment, the tubular closure device comprises a tubular sheath, wherein said tubular sheath encases at least a portion of the sealing tube.

In one embodiment, the tubular closure device comprises a nose cone sheath. In another embodiment, the nose cone sheath may encase at least a portion of the nose cone, the pusher cable and/or the plurality of anchors.

In one embodiment, the length of the anchor ranges from 0.25 to 20 mm.

In one embodiment, the tube is comprised of a biologic material. In another embodiment, the biologic material is pericardium or other biological membrane. In yet another embodiment, the biologic material has a sheet structure. In one embodiment, the sheet structure is derived from skin. In still another embodiment, the sheet structure is derived from a biological tubular structure. In another embodiment, the biological tubular structure is der such as those derived from skin, or tubular biological structures such as those derived from blood vessels, intestinal tissue, etc. In yet another embodiment, the tube is comprised of a synthetic material. In another embodiment, the sheet In still another embodiment, the synthetic material is, for example, a material identified by a trade name selected from Nylon®, Dacron®, or Teflon®, or is expanded polytetrafluoroethylene (ePTFE), and/or other materials. In a preferred embodiment, the sheet would be made from a bioabsorbable material.)

In one aspect, a method for closing a puncture wound comprising attaching a sealing tube to tissue surrounding the puncture wound is provided.

In one embodiment, the puncture wound is located in the wall of a blood vessel or the wall of a heart chamber.

In one embodiment, the tubular closure device is advanced through a trocar.

In one embodiment, the method comprises advancing the tubular closure device in a distal direction to the puncture wound. In another embodiment, the tubular closure device is advanced until the distal end of the device is located past the puncture wound. In another embodiment, the tubular closure device is advanced until the distal end of the device is located in the chamber of the heart or the lumen of the vessel.

In one embodiment, the pusher cable is pushed in a distal direction until the plurality of pusher arms radially expand away from the longitudinal axis of the tubular sealing device. In another embodiment, the nose cone is pushed in a distal direction to uncover the plurality of pusher arms, whereupon the pusher arms expand radially away from the longitudinal axis of the tubular sealing device.

In one embodiment, the method further comprises pulling the pusher cable in a proximal direction until the external surface of the sealing tube end portion contacts the luminal surface of the tissue surrounding the access point. In another embodiment, the pulling the pusher cable in a proximal direction causes the anchor stakes to enter the tissue surrounding the access point.

In one embodiment, the method further comprises pushing the pusher cable in a distal direction to release the anchor stakes from the pusher arms. In another embodiment, the method further comprises pulling the nose cone sheath in a proximal direction until the nose cone sheath encases the pusher arms and holds the pusher arms in a compact position.

In one aspect, a spiral closure device (spiral suture device) is provided.

In one embodiment, the spiral closure device comprises a spiral needle in the shape of a corkscrew, helix or spiral. In another embodiment, the distal end of the spiral needle comprises a pointed end. In yet another embodiment, the spiral needle is hollow.

In one embodiment, the spiral closure device further comprises an outer sheath and an inner sheath. In another embodiment, the internal surface of the outer sheath is threaded. In yet another embodiment, the external surface of the inner sheath is threaded.

In one embodiment, the inner sheath comprises a handle. In another embodiment, the outer sheath comprises a handle.

In one embodiment, the proximal end of the inner sheath is located proximal to the proximal end of the outer sheath.

In one embodiment, the spiral closure device comprises an inner sheath attached at its distal end to the distal end of the external sheath and which extends in a proximal direction beyond the proximal end of the inner sheath.

In one embodiment, the spiral needle forms a spiral along the longitudinal axis of the outer surface of the inner sheath. In another embodiment, at least a portion of the spiral needle is attached to at least a portion of the inner sheath. In another embodiment, the pitch of the spiral needle is approximately the same as the pitch of the inner sheath and the pitch of the threads of the inner sheath is approximately the same as the pitch of the threads of the outer sheath.

In one embodiment, the spiral closure device further comprises a suture encased at least partially by the spiral needle, wherein the spiral needle is hollow. In another embodiment, the suture may be a wire, line or cable. In yet another embodiment, the suture is bioabsorbable. In another embodiment, the proximal end of the suture line extends distal to the proximal end of the inner sheath. In still another embodiment, the spiral closure device further comprises a suture cap, wherein the suture cap is reversibly attached to the distal end of the spiral needle.

In one embodiment, the suture further comprises as least one barb or other anchoring element. In another embodiment the at least one barb is comprised a material which is the same as the material of the suture. In yet another embodiment, the at least one barb is comprised of a material which is different from that of the suture.

In one embodiment, the free end of a barb at the distal end of the suture points in approximately a proximal direction. In another embodiment, the free end of one or more barbs attached proximal to the barb at the distal end of the suture each point in a distal direction.

In one embodiment, the spiral closure device further comprises a suture reversibly attached at its distal end to the distal end of the spiral needle. In another embodiment, the suture reversibly attached to the distal end of the spiral needle via a second needle. In another embodiment, the spiral closure device further comprises a suture cap, wherein the suture cap is reversibly attached to the distal end of the spiral needle. In still another embodiment, the cap is reversibly attached to a cap wire, wherein the cap wire is unattached from the cap after positioning the suture.

In one embodiment, the distal end of the outer sheath comprises an opening through which the distal end of the spiral needle can pass.

In a one aspect, a method of suturing a tissue is provided.

In one embodiment, the distal end of the spiral closure device spiral needle is pushed along a spiral path through tissue which has been punctured or severed. In another embodiment, the spiral needle is pushed along the spiral path by rotating the handle of the inner sheath. In another embodiment, the spiral path surrounds all sides of the puncture or cut tissue and extends longitudinally along the puncture or cut. In yet another embodiment, the distal end of the spiral device spiral needle is pushed distally through approximately the entire depth of the tissue.

In one embodiment, after pushing the spiral needle through the tissue, the spiral needle is pulled in a proximal direction along the spiral path, whereby the spiral needle is removed from the tissue, but the suture remains secure within the tissue. In another embodiment, the suture is secured to the tissue via the at least one barb.

In one embodiment, the proximal end of the suture is pulled in a proximal direction to increase tension on the suture.

In one aspect, a tissue locating device is provided.

In one embodiment, the tissue locating device comprises one or more locating members, a straight wire member attached at its distal end to each of the one or more locating members, and a locating device sheath. In one embodiment, each of the one or more locating members is comprised a material selected from the group consisting of a shape memory metal and an alloy. In yet another embodiment, each of the one or more locating members may have a loop, a figure eight or an oval shape. In still another embodiment, the one or more locating members may be attached to or covered with a fabric piece.

In one embodiment, the straight wire member is a wire or cable. In another embodiment, the straight wire member is not straight and/or is flexible. In yet another embodiment, the one or more members may be fully or partially encased by the locating device sheath. In another embodiment, when the one or more members are not encased by the locating device sheath, the one or more members are in an expanded condition and positioned approximately 90 degrees with respect to the longitudinal axis of the tissue locating device. In another aspect, a single piece of fabric is attached to the one or more members.

In one aspect, a method for using a tissue locating device is provided.

In one embodiment, the method comprises, pushing the distal end of a tissue locating device in a distal direction through a tissue, wherein one or more locating members is encased by a locating device sheath; pulling the locating device sheath in a proximal direction independent of the plurality of locating members to unsheathe each of the one or more locating members, whereby each of the one or more locating members radially expands. In one embodiment, the method further comprises, pulling the tissue locating device in a proximal direction until the one or more locating members contact the internal surface of the tissue.

In one aspect, a tissue closure device is provided, comprising a spiral closure device and a tissue locating device.

In one aspect, a method for using a spiral closure device is provided.

In one embodiment, the method comprises: pushing the distal end of a tissue locating device through the tissue in a distal direction; pulling the locating device sheath of the tissue locating device proximally to unsheathe a plurality of members, whereby each of the plurality of members radially expands; and pulling the tissue locating device in a proximal direction until the plurality of members contact the internal surface of the tissue.

In one embodiment, the method further comprises: pushing a spiral closure device distally through the tissue by rotating in a first direction the handle of an inner sheath, whereby a hollow spiral needle which encases a suture, makes a spiral path through the tissue and surrounding the opening created by the locating device sheath, until the distal end of the hollow needed approximate meets the internal surface of the tissue; and rotating the handle of the inner sheath in a direction opposite the first direction to withdraw the hollow spiral needle from tissue, leaving the suture in place.

In one aspect, a tissue locating device comprising one or more adjustable arms, a fabric piece attached to a frame, wherein the frame has a central orifice and one or more arms, a threaded central member, a central connector fixed to the distal end of the threaded central member, an arm connector having two ends, wherein the first end is fixed to the central connector and the second end is fixed to the adjustable arm, and a first, second, and third rotational handle positioned near and attached to the proximal end of the threaded central member is provided.

In one embodiment, the distal end of the central member is positioned through the central orifice of the frame.

In one embodiment, the first rotational handle controls rotational and longitudinal movement of the threaded central member. In another embodiment, the second rotational handle functions to disconnect the distal end of the threaded central member from the central connector.

In one embodiment, the each of the one or more arms is attached at its proximal end to the central region of the frame via a movable hinge.

In one embodiment, the fabric piece is attached to each of the one or more arms such that the fabric pulls tight when the arms are in an extended position.

In one embodiment, the tissue locating device does not comprise the fabric piece.

In one aspect, a method for using the tissue locating device is provided, comprising starting with the frame in a collapsed position, wherein the arms are approximately parallel to the longitudinal axis of the tissue locating device, pushing the distal end of the tissue locating device through the tissue in a distal direction until the entire frame is located distal to the tissue; rotating the first rotational handle to move the threaded central member in a distal direction, whereby the one or more adjustable arms move to an expanded position perpendicular to the longitudinal axis of the device; pulling the tissue locating device in a proximal direction until the one or more arms abut the internal surface of the tissue; rotating the second rotational handle to disconnect the distal end of the threaded central member from the central connector; and pulling the first, second and third rotational handles with central member proximally to remove the handles and central member from the patient.

In one embodiment, the tissue locating device comprises a marker, wherein the marker allows a user to visualize the location of the device within the patient. For example, a metallic marker may be embedded or otherwise fixed to the tissue locating device which would indicate the distal position of the device within a patient. This marker could be visualized or referenced using fluoroscopy or echocardiography. If the spiral needle of the closure device is metallic, the spiral needle may function as a marker. Another means of visualizing the position of the closure device would be through the use of a radiopaque maker embedded or otherwise fixed to the device. Positioning would be monitored or determined using means such as an x-ray and/or echocardiography as is well understood by persons skilled in the art.

In one aspect, a vascular closure device is provided.

In one embodiment, the vascular closure device comprises a film of flexible bioabsorbable material, wherein the length is greater than the width. In another embodiment, the film is shaped as a rectangle.

In one embodiment, the thickness of the film ranges from about 0.01 mm to about 1.0 mm. In another embodiment, the length of the film ranges from about 2.0 cm to about 4.0 cm. In yet another embodiment, the width of the film ranges from about 0.2 cm to about 3.0 cm.

In one embodiment, the vascular device further comprises an insertion device which at least partially encases the film so that the film is folded over onto itself and the location of folding forms a loop. In one embodiment, the loop may vary in size prior to insertion into a blood vessel.

In one aspect, a method for using the vascular closure device is provided.

In one embodiment, the vascular closure device comprises inserting an insertion device through an opening in a vessel wall, wherein a rectangular shaped film is folded onto itself, the overlapping portions of the film are encased by the insertion device, and the position of folding of the film (the loop) is located distal to and approximately adjacent to the distal end of the insertion device; manipulating the insertion device to push the loop into the vessel interior such that the loop expands to contact and line the interior surface of the vessel wall; manipulating the insertion device to remove excess film which remains outside of the vessel; and pulling the insertion device proximally to remove the insertion device from the patient.

DRAWINGS

FIGS. 1-10 illustrate tubular sealing device components and methods for use.

FIGS. 12A-12B illustrate embodiments which provide a force that pushes a sealing tube end portion towards the tissue surrounding the access site.

FIGS. 20A-20B illustrate embodiments for a tissue locating device.

DETAILED DESCRIPTION

Closure devices and methods for their use for a variety of tissues, including vascular tissue, is described herein. As minimally invasive surgical procedures become increasingly common and more feasible, it becomes important to solve the more difficult problems. When such techniques, e.g., percutaneous procedures, are used, the surgeon is faced with the difficulty of closing the tissue using typical surgical procedures such as suturing or stapling. Thus, simple ways to close access points are needed for safe, effective and more cost-effective procedures.

One embodiment described below is a closure device that allows a practitioner to close an opening or wound when afforded only minimal access as in a percutaneous surgery. The device allows the practitioner to seal the opening with minimal damage to the surrounding tissue while also minimizing subsequent leakage after the procedure is complete. An example of a procedure which benefits from such a device is a transapical access for cardiac valve replacement, described in more detail below. It is understood that the devices described herein are also useful for closing puncture wounds or access points in blood vessels.

One embodiment described below is a device that allows a practitioner to close an opening or wound when afforded only minimal access as in a percutaneous surgery.

The Tubular Closure Device

A device, referred to as a tubular closure device, uses a hollow tube, which is sealed at one end, to prevent leakage of fluid from the heart or vessel. The open end of the hollow tube is attached to the luminal surface of the tissue surrounding the access site. The attached tube transverses the wall of the lumen or heart chamber such that the sealed end of the tube is located outside of the heart chamber or vessel wall.

The tube is comprised of a biologic material. The biologic material may be, but is not limited to, pericardium or another biological membrane. In general, the biologic material should have a sheet structure. This sheet structure may, for example, be derived from skin. Alternatively, the sheet structure could be derived from a biologic tubular structure such as a blood vessel, intestinal tissue.

The tube may alternatively be comprised of a biocompatible synthetic material. Such materials include, but are not limited to, Nylon®, Dacron®, and Teflon®. Another synthetic material to use for fabricating the tube may be expanded polytetrafluoroethylene (ePTFE) and/or other materials. In a preferred embodiment, the sheet is made from a bioabsorbable material.

Figure 1:
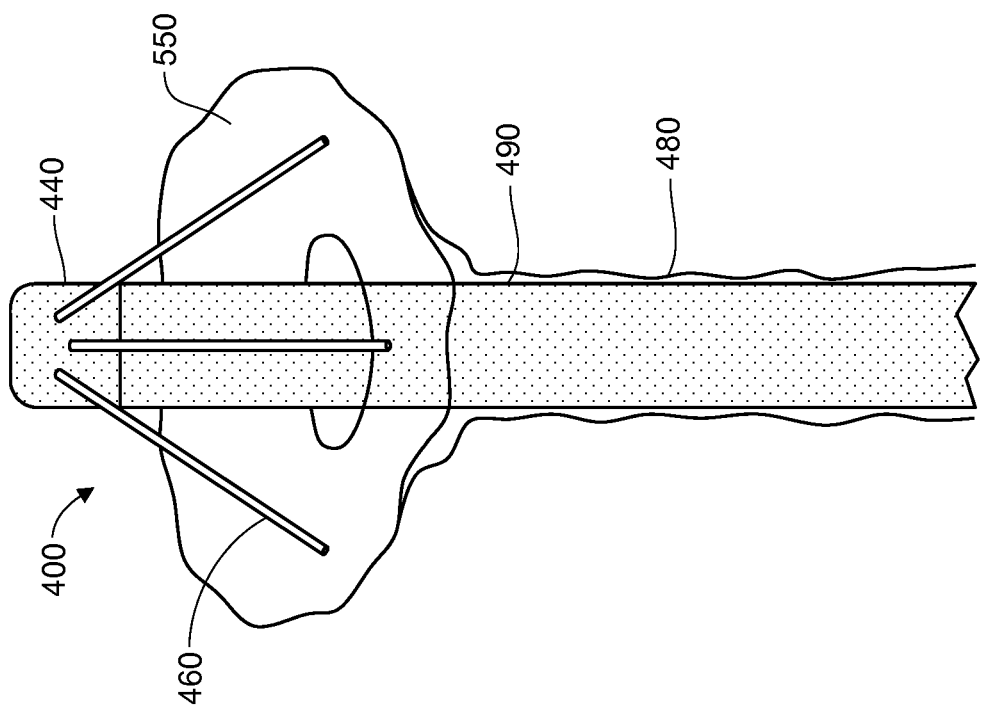

An exemplary embodiment of the tubular closure device is illustrated in FIGS. 1-10. FIG. 1 shows tubular closure device 400 which comprises a sealing tube 480, and pusher cable 490 and pusher arms 460. The distal terminus of pusher cable 490 may comprise a nose cone 440. The proximal side of nosecone 440 is associated with a pusher cable 490. In some embodiments, pusher cable 490 is hollow to allow, for example, a guidewire 540 to be fed through pusher cable 490 or to allow, for example, pusher cable 490 and the associated closure device to move along guidewire 540.

One end of each pusher arm 460 is attached to the distal terminus of pusher cable 490 or nose cone 440. The attachment of pusher arms 460 is flexible to allow pusher arms 460 to be in a compact position wherein each lies approximately parallel to the longitudinal axis of tubular closure device 400, or in an expanded position in which each pusher arm 460 extends radially from the longitudinal axis of tubular closure device 400. It is understood that the number of pusher arms 460 may vary greatly. Pusher arms 460 may be any feature or element which essentially pushes or applies a force to the inner surface of the distal portion of sealing tube 480 against the luminal tissue surrounding the access site. Additional embodiments which provide this force are described in more detail below.

FIG. 1 also illustrates that the distal end of sealing tube 490 flares radially from the longitudinal axis. This flared portion is referred to herein as a sealing tube end portion 550. Note that sealing tube 480 has many folds when it is packed into sheath 430. Accordingly, when the distal (first) end of sealing tube 480 is pushed out of sheath 430, the distal edge of sealing tube 480 can flatten out over the tissue or vessel wall surrounding the puncture. It is understood the further sealing tube 480 is pushed distally past the puncture, the larger the surface area of tissue surrounding the puncture. The portion of sealing tube 480 which is flattened against, or which will be flattened against, the tissue or vessel surrounding the puncture will be referred to herein as sealing tube edge 550. It is understood that sealing tube 480 is pliable, thus allowing the flaring to occur. When sealing tube 480 is properly attached to the access site to prevent leakage of fluid from the access site, the outer surface of sealing tube end portion 550 is securely attached or fastened to the luminal surface of the vessel wall or heart chamber tissue surrounding the access site.

Figure 2:
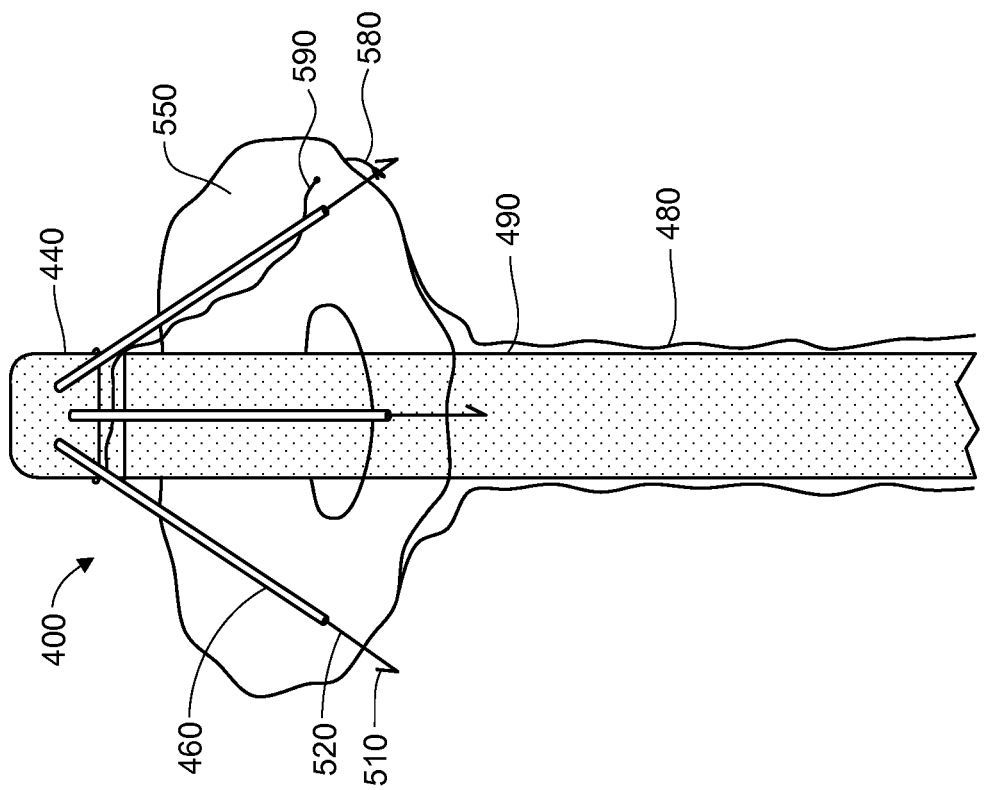

FIG. 2 illustrates another embodiment wherein each of pusher arms 460 is hollow and encases an anchor stake 520. Anchor stake 520 may comprise one or more barbs 510 or other structure which facilitates attachment of sealing tube end portion 550 to the vessel or chamber tissue. FIG. 2 also illustrates the condition of device 400 prior to delivery of sealing tube 480 to the access site. Specifically, in the particular embodiment, anchor stakes 520 are pierced through sealing tube end portion 550. In addition, one of anchor stake 520 is attached to a suture 590 via a suture knot 580.

FIG. 3 illustrates tubular closure device 400 prior to delivery of sealing tube 480, wherein said sealing tube device is encased within a sheath 430. Sheath 430 functions to hold sealing tube device 400 in a compact condition to allow delivery, for example, through a trocar to the access site. Pusher arms 460 are in a compact position such that they are compressed against pusher cable 490. Anchor stakes 520 are pierced through sealing tube end portion 550. The free terminus of each anchor stake 520 comprises optional barb 510.

FIG. 4 shows tubular closure device 400 in an expanded configuration in which the distal end of device 400 has been advanced distally such that sealing tube end portion 550 is in a position distal to the distal edge of sheath 430. Pusher arms 460 are in an expanded position such that they are extended radially from the longitudinal axis of device 400. Anchor stakes 520 are pierced through sealing tube end portion 550. The free terminus of each stake 520 comprises optional barb 510. Suture 560 is tied to the distal end of at least one stake. Suture 560 is threaded through sealing tube end portion 550 and attached to a position on nose cone 440 (or it may be attached to a position on pusher cable 490). Barbs may be any physical feature which facilitates anchoring of anchor stakes 520 to the tissue. In one embodiment, the barbs are staples.

Figure 5:
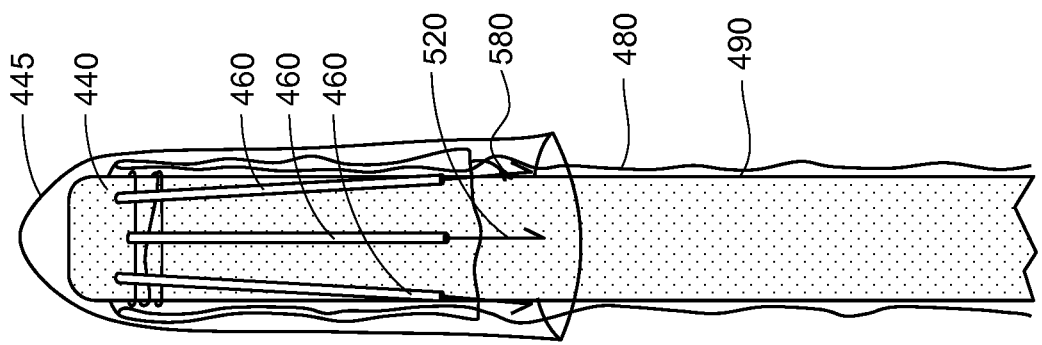

FIG. 5 illustrates device 400 after release of anchor stakes 520 from pusher arms 460. In situ, each of anchor stakes 520 have entered the tissue surrounding the access point to fasten sealing tube end portion 550 to the surrounding tissue. Furthermore, suture 590 is detached from suture knot 580.

Figure 6:
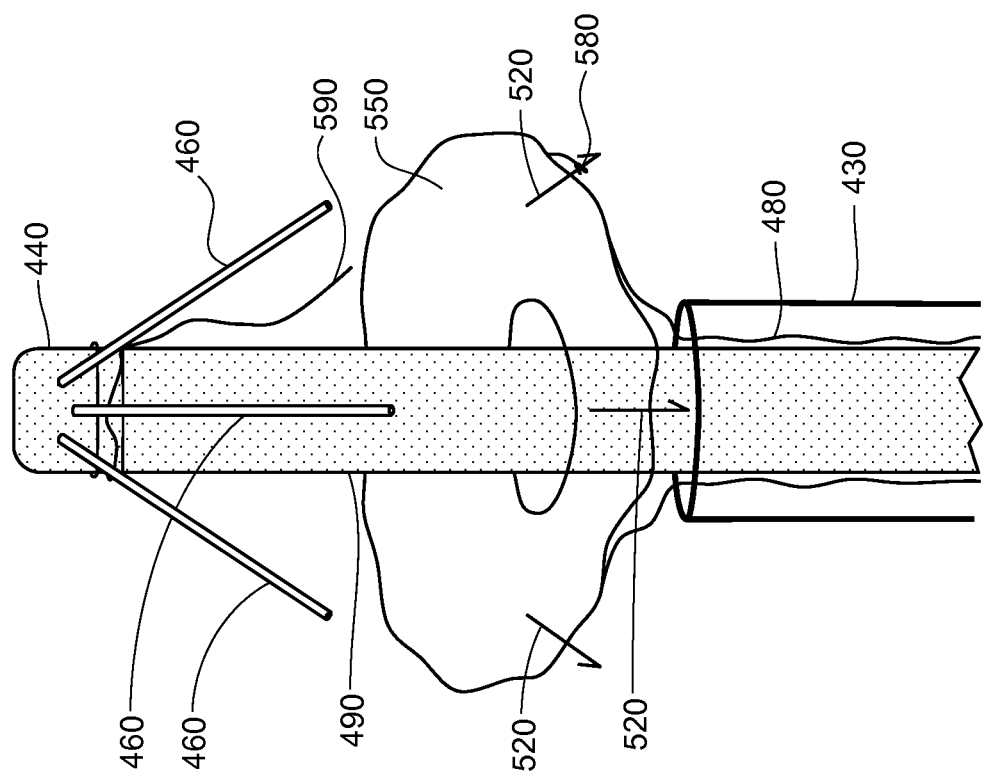
Figure 7:
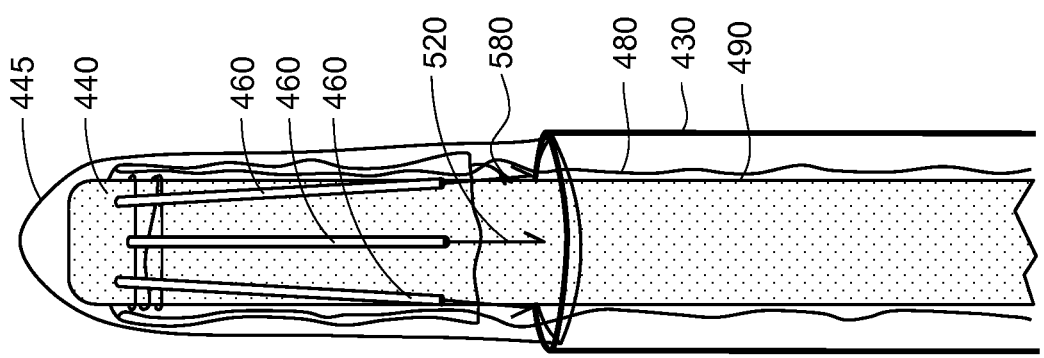

FIG. 6 illustrates an embodiment of device 400 wherein the device comprises a nose cone sheath 445. Nose cone sheath 445 serves to maintain pusher arms 460 in a compact position both prior to and after delivery of sealing tube 490. Nosecone sheath 445 maintains the distal end of closure device 400 in a compact condition, facilitating removal of closure device 400 after attachment of sealing tube end portion 550 to the tissue surrounding the access site. FIG. 7 illustrates yet another embodiment of device 400 wherein the device further comprises a sheath 430 which encases at least a portion of sealing tube 480.

In one embodiment, device 400 may comprise sheath but no nose cone (FIG. 5), in which case, the distal ends of pusher arms 460 and/or anchor stakes 520 are encased within the sheath 430 to hold them in a compact or compressed position.

Figure 8:
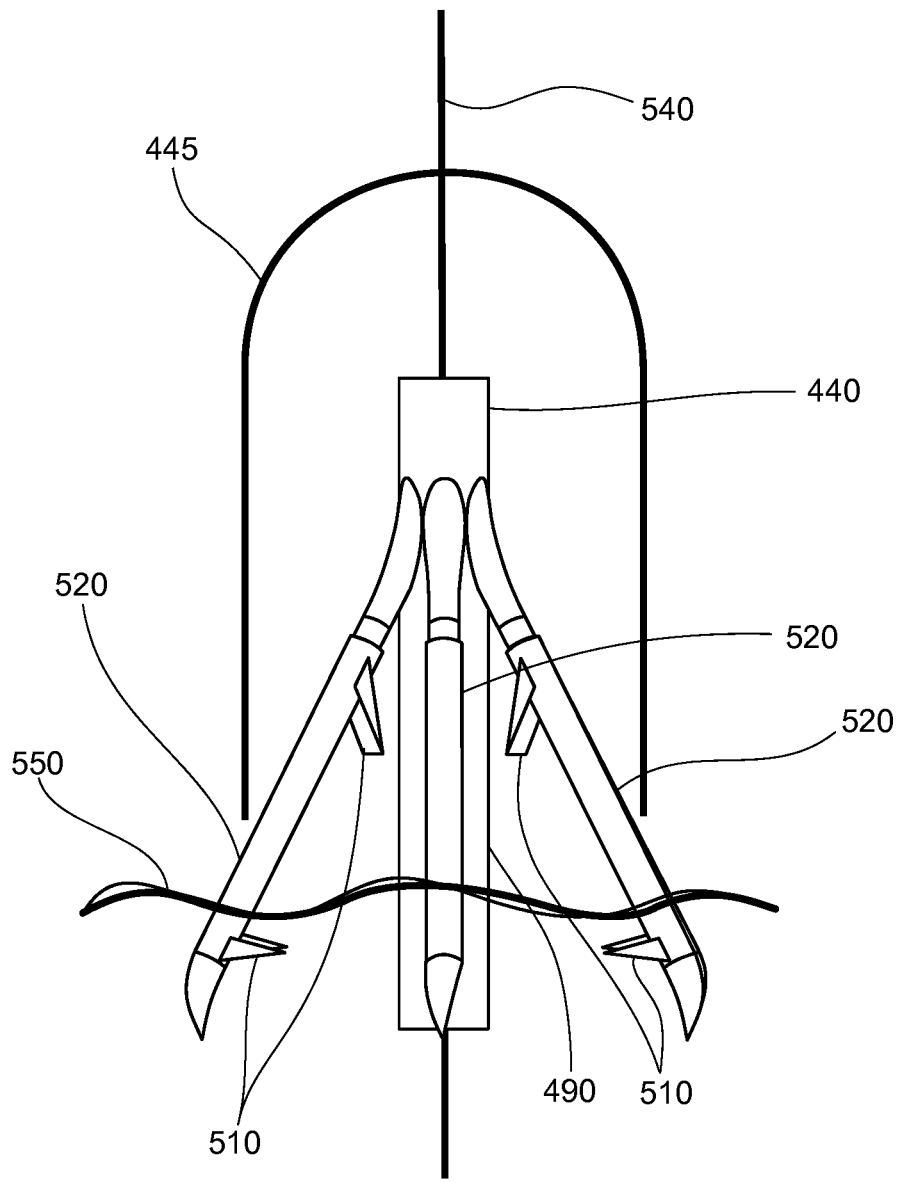

FIG. 8 shows an alternative embodiment with respect to pusher arms 460 and anchor stakes 520. Anchor stakes 520 are hollow, allowing them to be reversibly associated with pusher arms 460 by encasing the pusher arms. In one embodiment, barbs 510 would be on the external face of anchor stakes 520. Here, barbs 510 would be able to bend on pusher arms 460 when the pusher arms are in a compact position, e.g., packed within nose cone 445. Upon removal of the device, anchor stakes 520 detach from pusher arms 460 and remain in the tissue. When anchor stakes 520 are released from pusher arms 460, anchor stakes 520 move in a radial direction. Device 400 further comprises a barb sheath which encases anchor states 50 and barbs 510. The barb sheath can maintain barbs 510 in a compact position abutted with pusher cable 460.

Figure 9:
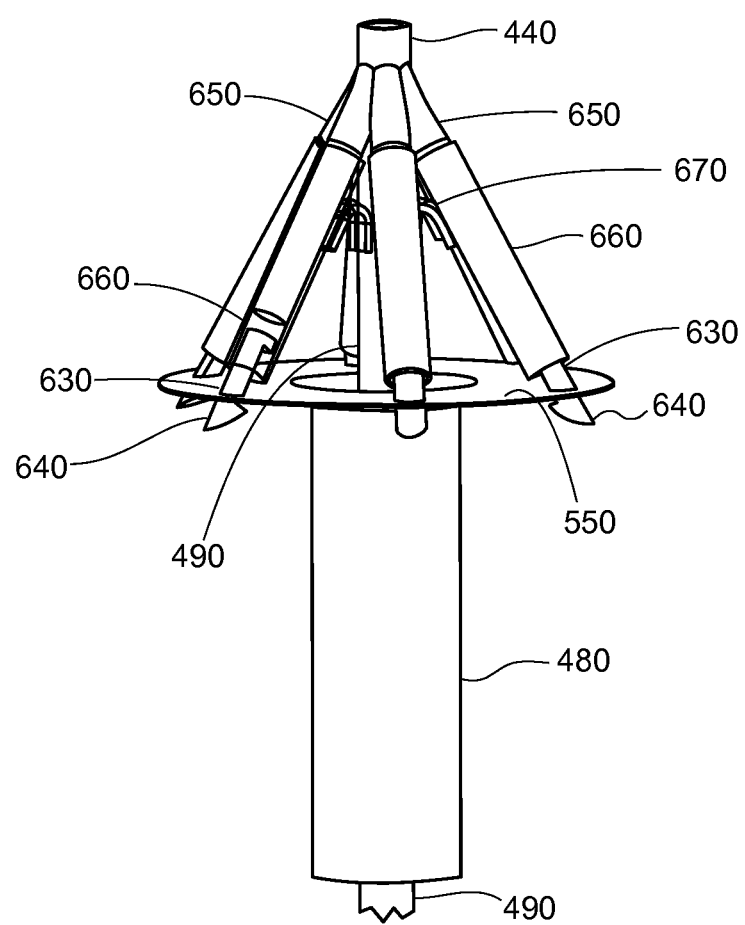

FIG. 9 shows still another embodiment with respect to the configuration of pusher arms and anchor stakes. In this embodiment, anchor stakes 630, which may comprise at least one barb 640, are positioned distal to pusher arm 650 and anchor stake 630 is encased in a pusher arm sheath 660. Pusher arm sheath 660 may be comprised of a variety of materials such as a rigid metal or plastic. A flexible linker 670 which fastens pusher arm sheath 660 to pusher cable 490. Flexible linkers 670 allow pusher arms 650 and anchor stakes 630 to be maintained in a compact or expanded position.

Figure 10:
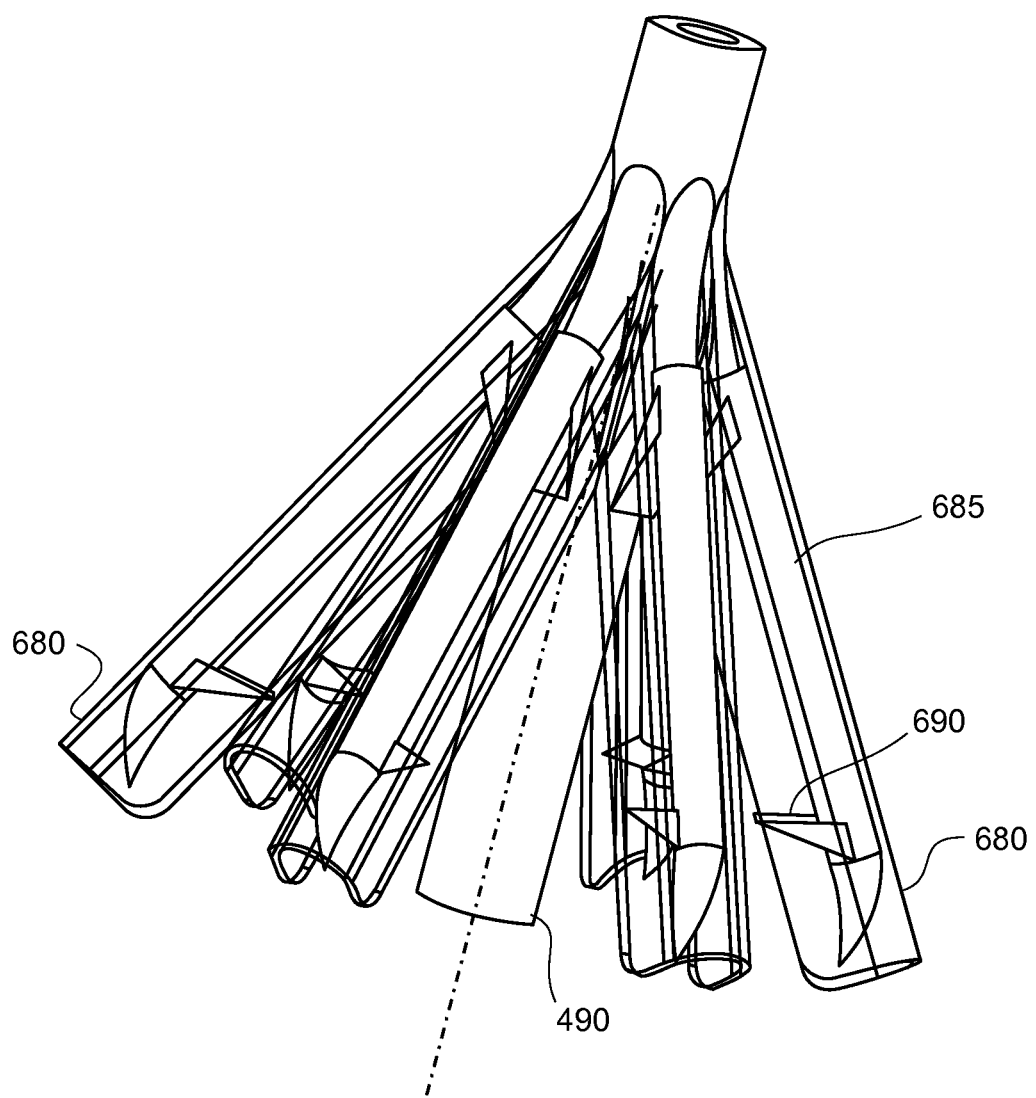

FIG. 10 illustrates an embodiment wherein an open-sided sheath (guard 680) is used to partially encase the anchor stakes 685 comprising barbs. The open-sided sheath and anchor stakes bend together. The design of the open-sided sheath allows the barbs to easily extend. In one embodiment, barbs 690 are pushed through the sealing tube end portion and then guard 680 is pushed over barbs 690.

Figure 11B:
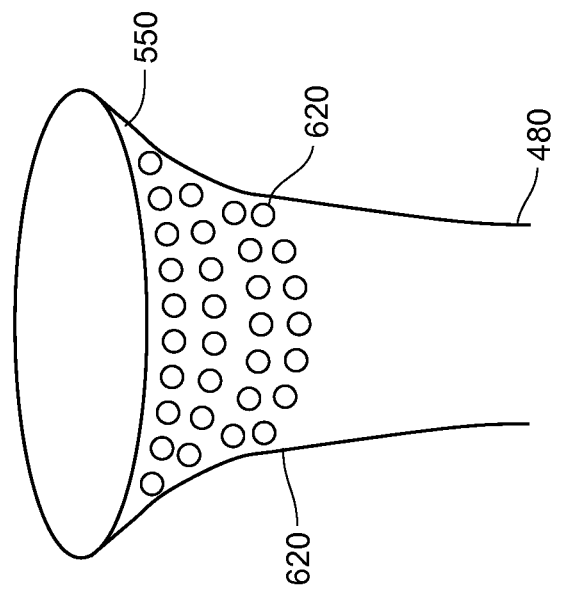
FIGS. 11A-11B illustrate embodiments for sealing a sealing tube to surrounding tissue.
Figure 11A:
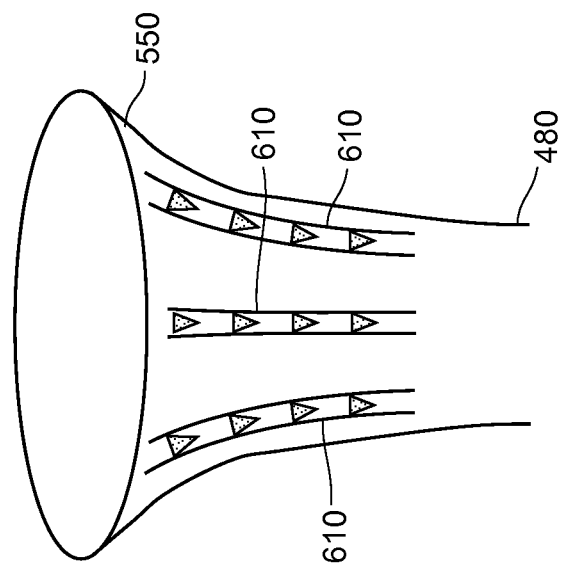

FIGS. 11A-11B show alternative embodiments for fastening sealing tube end portion 550 to the tissue surrounding the access site. In one embodiment, as shown in FIG. 11A, a plurality of suction cups are fastened to the outer surface of sealing tube end portion 550. In a second embodiment, shown in FIG. 11B, a barb strip 610 is constructed in which a series of barbs are secured to a strip of material. Barb strip 610 is then secured to the outer surface of sealing tube end portion 550.

FIGS. 12A-12B illustrate alternative embodiments which provide a force that pushed sealing tube end portion 550 towards the tissue surrounding the access site. As shown in FIG. 12A, a balloon 600 may be inflated. Balloon 600 is attached to a controller at the proximal end of the tubular sealing device so that balloon 600 can be pulled in a proximal direction to push sealing tube end portion 550 towards the tissue. Similarly, a split tube 630, can be attached to a controller at the proximal end of the tubular sealing device. Pulling split tube 630 will result in deformation of the split tube as shown in FIG. 12B, thereby providing a surface which may push on sealing tube end portion 550 until it contacts the surrounding tissue.

Figure 13C:
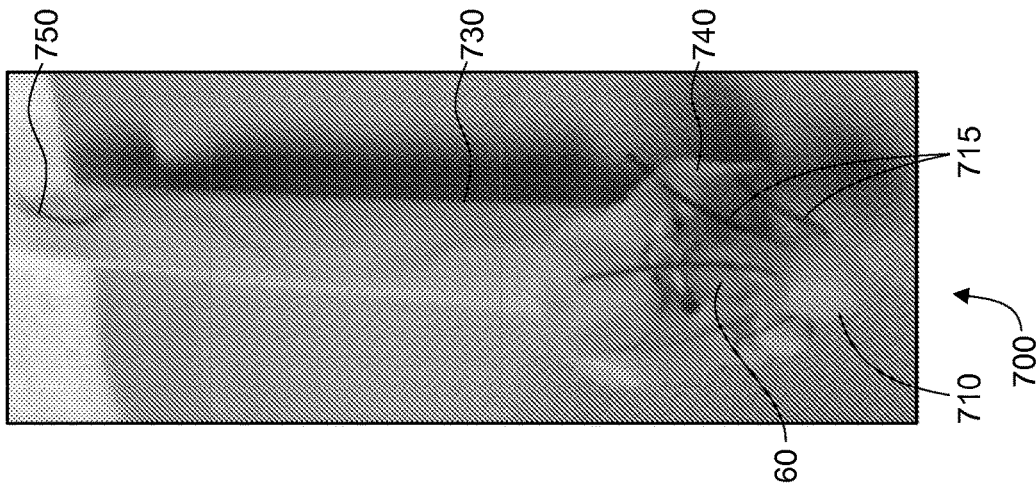
FIGS. 13A-13C are photographs of an embodiment of a tubular sealing device.
Figure 13B:
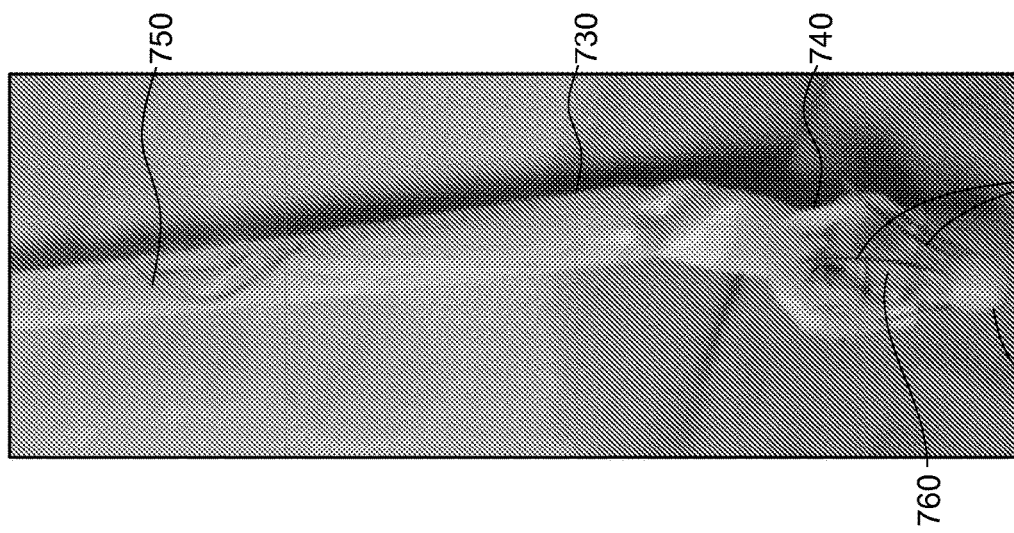
Figure 13A:
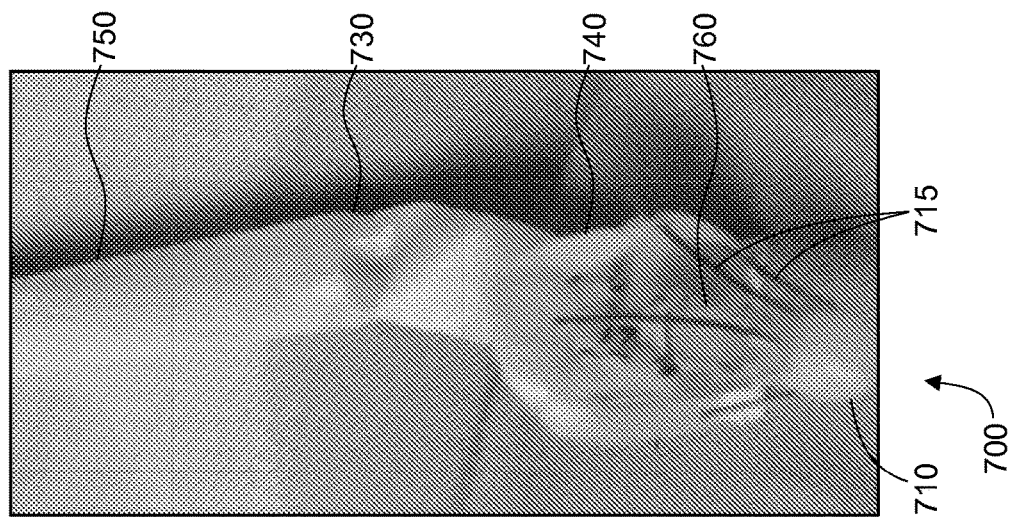

FIGS. 13A-13C are photographs of a tubular sealing device. In these photographs, a pericardial tube is packed within a sheath. Seen best in FIG. 13B is a suture which has been used to suture a length of the pericardial tube. One end of the suture has been threaded through the distal end portion of the pericardial tube and is attached to the pusher cable.

Figure 14A:
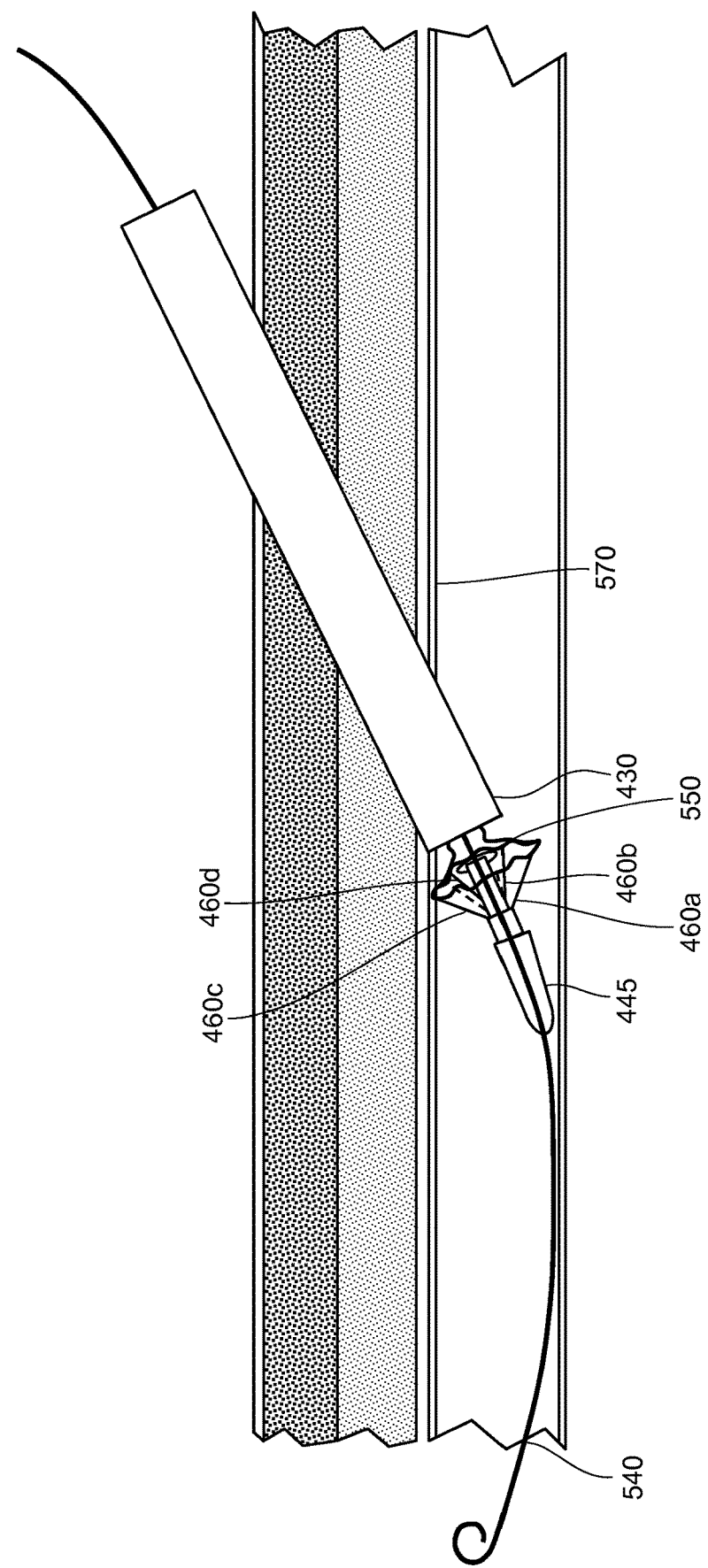
FIGS. 14A-14C are embodiments of a tubular sealing device.
Figure 14B:
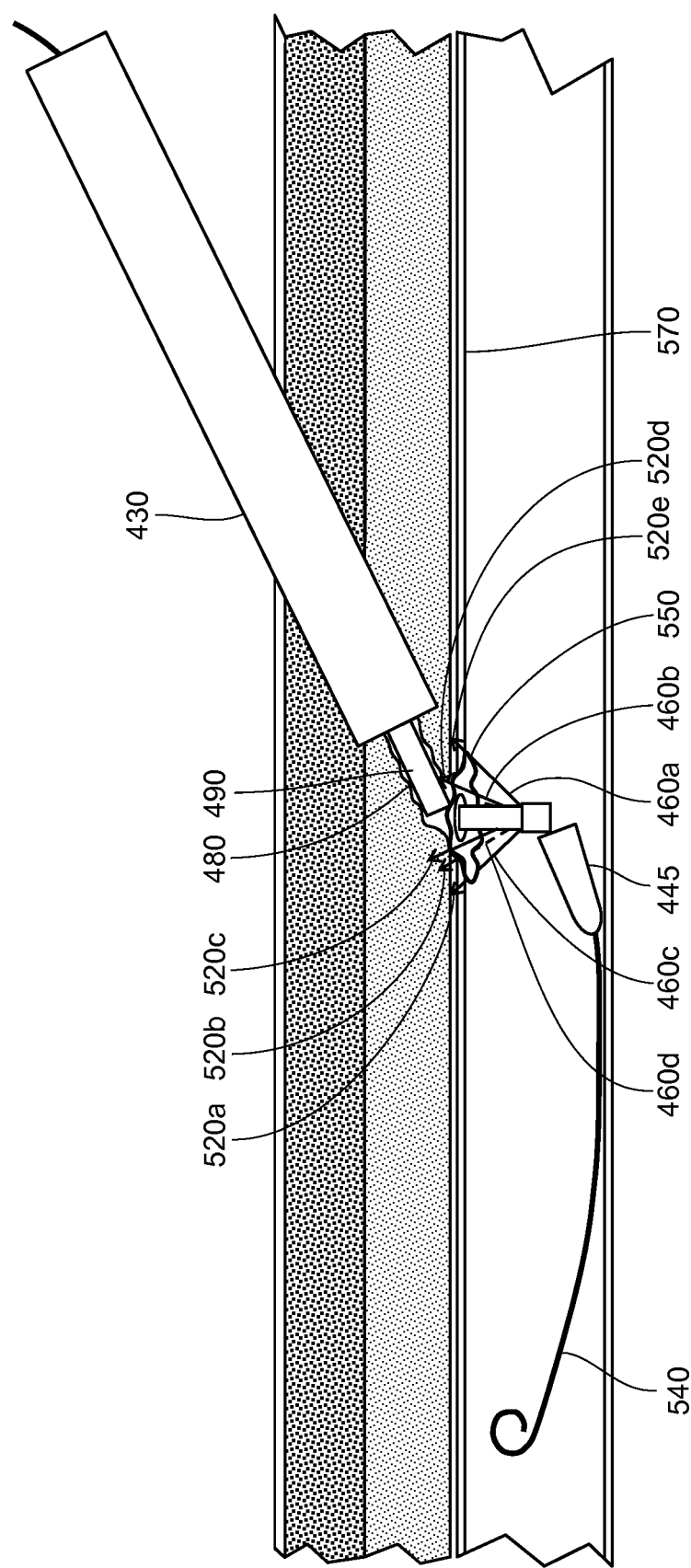
Figure 14C:
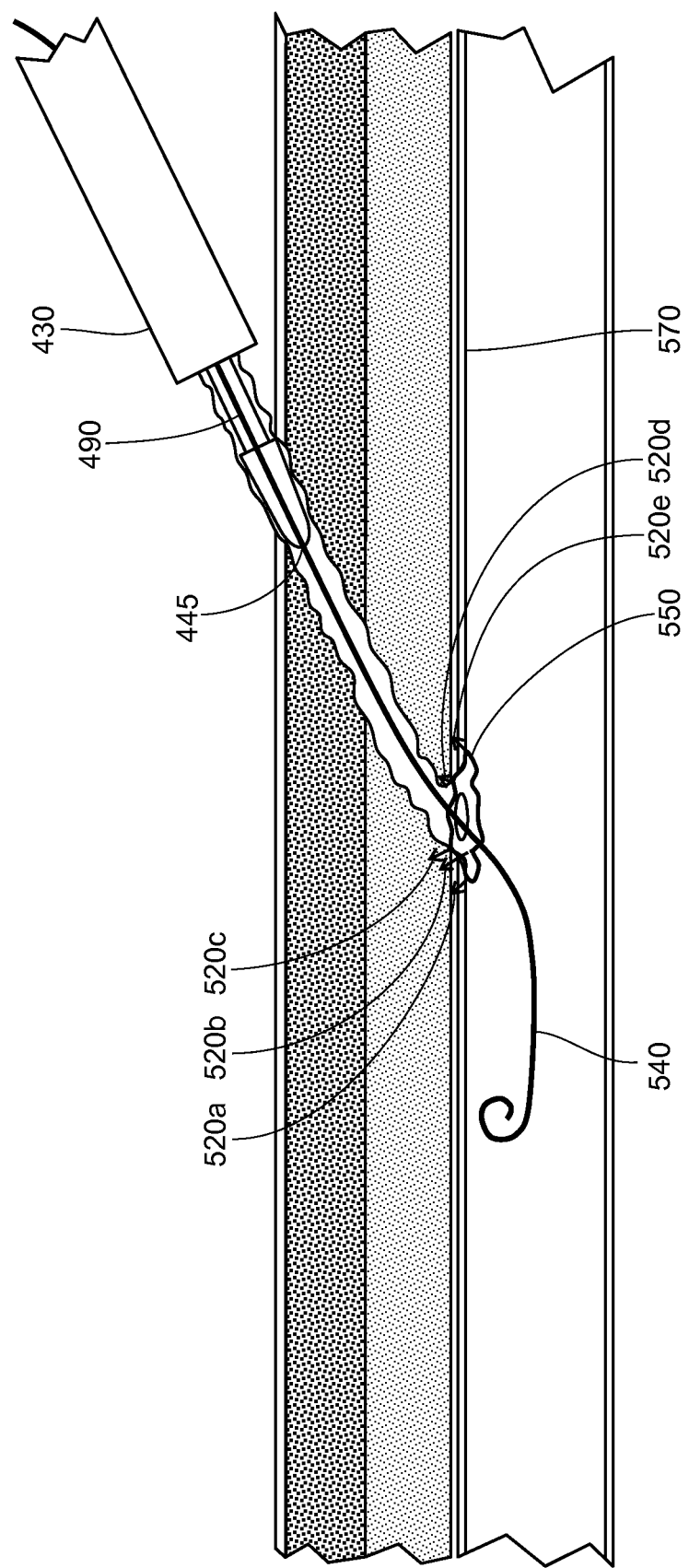

Methods for using tubular sealing device 400 are also provided herein. One such method is illustrated in FIGS. 14A-14C. When device 400 is delivered to the access or puncture site, it is in a compact condition encased at least in part by sheath 430. Guidewire 540 can be threaded through hollow pusher cable 490. Device 400 and sheath 430 are advanced distally until the distal ends of device 400 and sheath 430 are through and past the punctured tissue of the vessel wall or heart chamber wall, for example.

Device 400 is advanced in a distal direction while sheath 430 is held steady (not advanced). As a result, the distal end of nose cone 445 advances along guidewire 540 past the distal edge of sheath 430. As seen in FIG. 14A, nose cone 445 of device 400 is advanced in a distal direction while both pusher cable 490 and sheath 430 are held steady (not advanced). As a result, pusher arms 460a-d expand radially away from the longitudinal axis of device 400. It is understood that there may be any number of pusher arms in a particular device.

Sheath 430 is then pulled in a proximal direction to uncover more of sealing tube 480. Then, sheath 430 is held steady while nose cone 440 is pulled in a proximal direction toward the access site. Nose cone 440 is pulled in a proximal direction until sealing tube edge 550 contacts the luminal surface of tissue wall 570 surrounding the access site.

As illustrated in FIG. 14B, anchor stakes 520 are pushed away from and out of pusher arms 460 and into the tissue surrounding the puncture. In this embodiment, barbs 510 are shown at the distal terminus of each anchor stake 520.

After anchor stakes 520 have secured sealing tube end portion 550 to the surrounding tissue, nose cone sheath 445 is pulled in a proximal direction to encase pusher arms 460 in order to compress pusher arms 460 into a compact position. The compact device 400 can now be pulled in a proximal direction to remove the device from the tissue, while leaving sealing tube 480 in place, transversing the wall of the heart chamber or vessel (FIG. 14C). After removal of device 400, sealing tube remains.

The Spiral Closure Device

In another aspect, a device, referred to as a spiral closure device, allows the surgeon to thread a suture line through tissue surrounding a tissue puncture. An example of a procedure which benefits from such a device is a transapical access for cardiac valve replacement, described in more detail below.

Figure 15A:
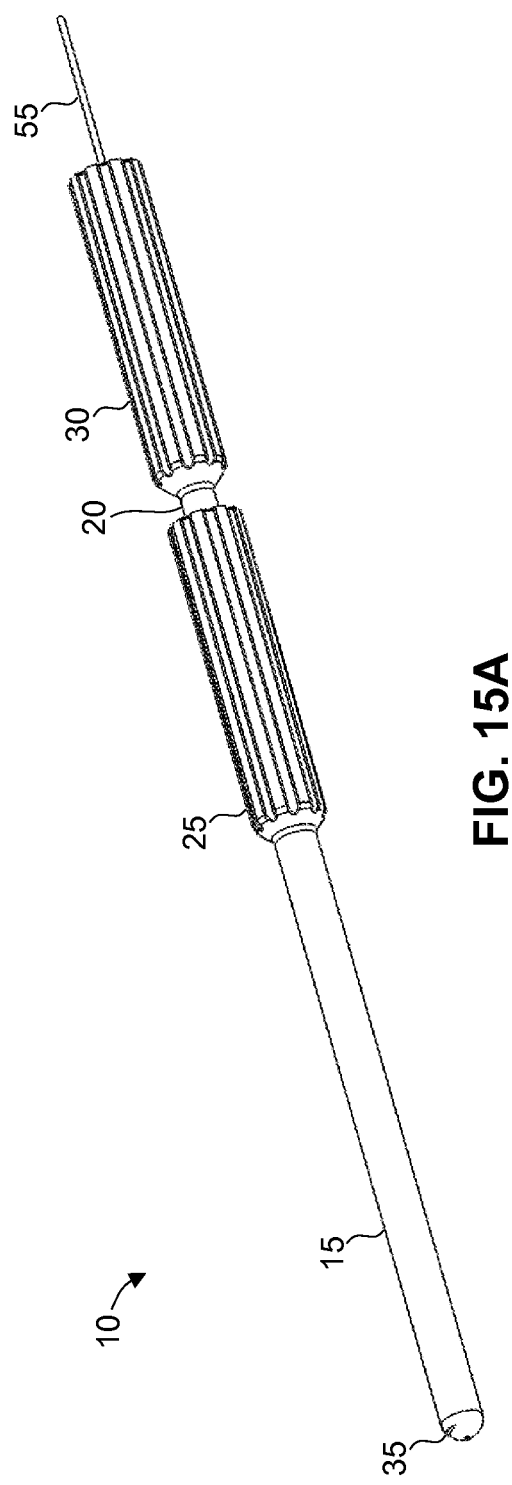
FIG. 15A-15E illustrate various embodiments of a spiral closure device.
Figure 15B:
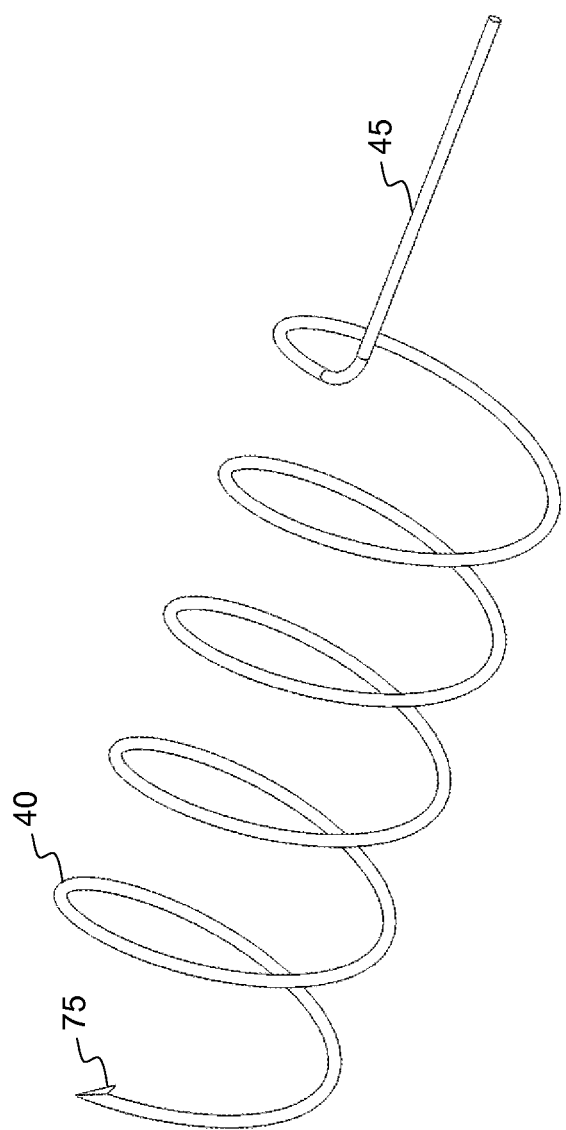
Figure 15C:
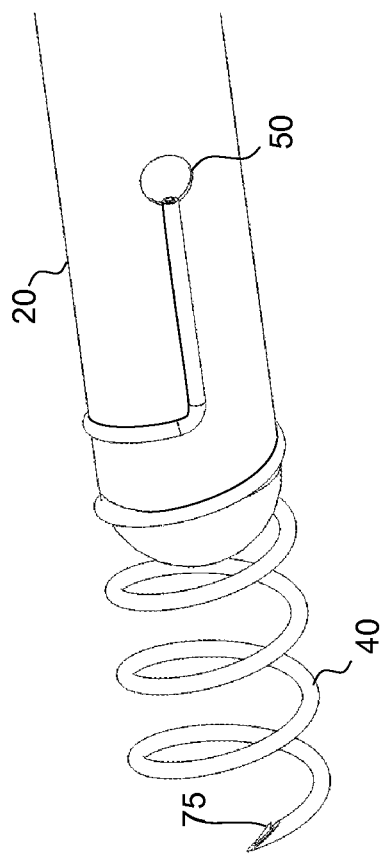

An exemplary embodiment of spiral closure device 10 is illustrated in FIG. 15A-15C. The spiral closure device is a cylindrical device comprised of an outer sheath 15 and an inner sheath 20. The outer sheath partially encases the inner sheath, however the distal end of the outer sheath lies distal to the distal end of the inner sheath. The outer sheath and the inner sheath have an outer sheath handle 25 and an inner sheath handle 30, respectively. The distal end of the outer sheath has an opening 35, through which a spiral needle 40 may be threaded. FIG. 15B illustrates the spiral needle which is fixed or attached to the distal end of the inner sheath. The distal portion of the spiral needle has a spiral or corkscrew shape and ends in a sharp point to allow easy piercing of the tissue. The proximal end of spiral needle 40 comprises a straight portion 45, which extends proximally through the inner sheath and beyond the proximal end of the inner sheath.

FIG. 15C shows how the proximal region of spiral needle 40 is fixed to the external surface of the distal portion of inner sheath 20. A hole 50 in the wall of the inner sheath provides an opening through which a suture may be threaded into the hollow shaft of the inner sheath.

In one embodiment, a suture is reversibly attached at its distal end to the distal end of the spiral needle. In this embodiment, the spiral needle may or may not be hollow. The suture is positioned external to the needle but may enter the central sheath through a hole within the wall of the central sheath. Moreover, the distal end of the suture is reversibly attached to the spiral needle such that the spiral needle can be retracted, leaving the suture in place. The length of suture extending from the proximal end of the inner sheath can vary as needed. The suture can be made of any one of many materials known to those having skill in the art. In one embodiment, the suture is made of a bioabsorbable material.

In another embodiment, the suture is reversibly attached to the distal end of spiral needle by a second suture needle. A cap may be positioned over suture 85 and second suture needle 95, although it is understood that the cap may be present over the distal tip of the needed when the suture is attached to spiral needle in the absence of a second suture needle. A second suture (or other comparable flexible material including, but not limited to, a wire or cable) can be reversibly attached to the cap. In this embodiment, after the suture is positioned through the tissue to be closed, the second suture can be unattached from the cap and removed from the patient with the spiral needle and closure device.

Figure 15D:
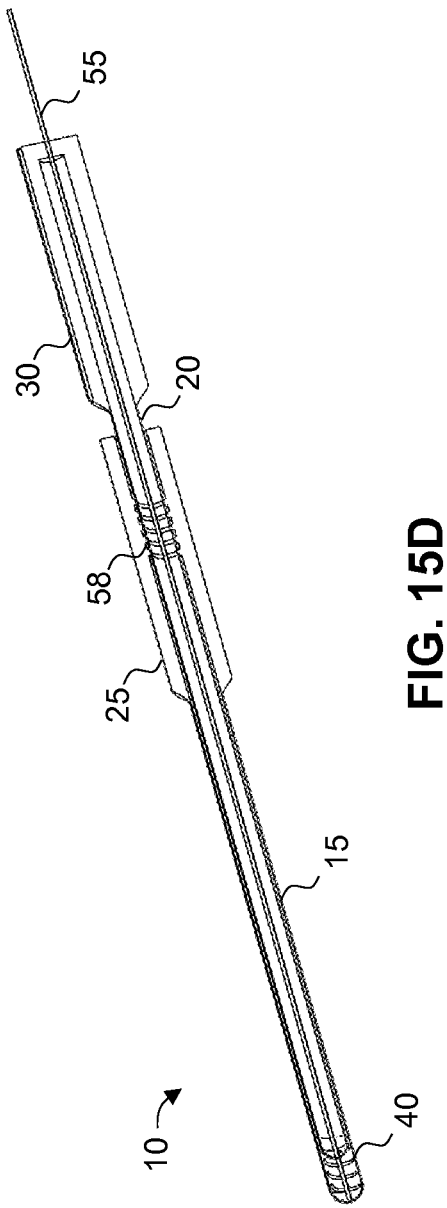

FIG. 15D is a cross-sectional view of spiral closure device 10. Spiral needle 40 is positioned within the distal portion of outer sheath. In some embodiments, the spiral closure device may further comprise a central sheath 55 which is attached at its distal end to the internal face of the distal end of outer sheath 15. Central sheath 55 extends proximally through the distal end of inner sheath 20, through the length of inner sheath 20 and out the proximal opening of inner sheath 20. In other embodiments, threads 58 between the inner and outer sheaths may be at the same pitch as the hollow spiral needle so that the spiral needle can be moved along the longitudinal axis based on the threading between the handles of the inner and outer sheaths, rather than based on the threading of the spiral needle.

Inner sheath 20 can be turned to rotate spiral needle 40 as it simultaneously moves along the longitudinal axis. For example, inner sheath handle 30 can be turned in a clockwise direction to move spiral needle 40 in a distal direction. Spiral needle 40 is positioned so that it will thread out though opening 35 at the distal end of outer sheath 15. Outer sheath 15 also has an opening at its distal tip which is connected to central sheath 55. A guidewire, for example, may run through this opening and the central sheath.

Figure 15E:
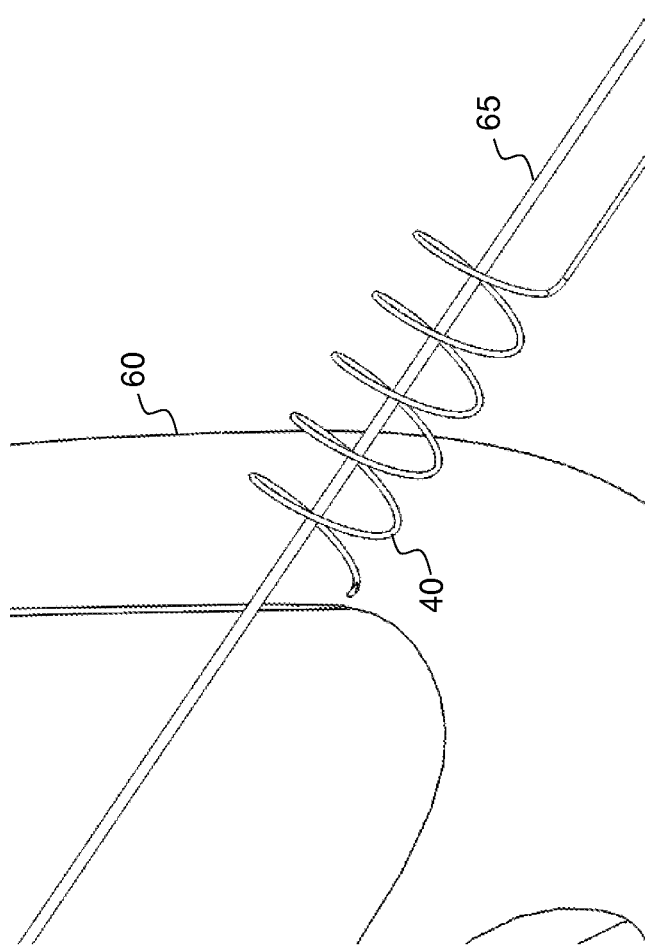

FIG. 15E illustrates spiral needle 40 positioned within the wall of the left ventricle of the heart (shown as 60). A guidewire is depicted as 65.

A hollow spiral needle of the spiral closure device encases a suture. The suture can be made of any number of materials as is appreciated by persons having ordinary skill in the art. The suture can be a thread, wire, cable or line made from suture material standard in the practice. Prior to introduction of the spiral closure device into the tissue, the distal end of the suture is positioned at the distal opening of the hollow wire. A suture can be encased within a such as spiral needle 40 shown in FIG. 15E. The distal end of suture 70 terminates in an anchor barb 75. The free end of the anchor barb may point in a proximal direction. In some embodiments, there is a plurality of anchor barbs located near the distal terminus of the suture. In other embodiments, all anchor barbs are oriented in the same direction.

In some embodiments, a plurality of accessory barbs are present along the length of the suture. The direction of each of the plurality of accessory barbs along the length of the suture would be oriented in a direction opposite that of the anchor barb(s) present at the distal terminus of the suture. This prevents the suture from relaxing when tension is applied to the proximal end of the suture.

To use the spiral suture device, the distal end of the outer sheath is placed adjacent to the external surface of the tissue, where the opening to be sutured is located. The inner sheath handle is then rotated while the outer sheath is held stationary. As a result, the distal tip of the spiral needle comes out through the opening of the outer sheath and pierces the tissue. Continued rotation of the outer sheath in the same direction results in the spiral needle threading along a spiral or helical path through the tissue. This threading is continued until the distal end of the spiral needle is located approximately at the inner surface of the tissue. In some embodiments, the distal end of the spiral needle is threaded until it has penetrated one-half or three-quarters of the depth of the muscle tissue.

At this time, the inner sheath handle is rotated in the opposite direction. The anchoring barb or barbs catch onto the tissue to secure the suture. The inner sheath handle is further rotated to move the spiral needle along the same spiral path in a proximal direction until the spiral needle is completely removed from the tissue. The suture, which may also have accessory barbs along its length, is secured along a spiral path to the muscle tissue at points surrounding the tissue opening.

At this time, the spiral suture device can be removed from the patient, leaving the suture in place within the tissue.

Tissue Locating Device

Successful and efficient use of the spiral suture device depends on the ability to thread the spiral needle through the tissue to an appropriate depth. The tissue locating device also aids in approximating the starting location of the insertion of the helical needle and suture. This is accomplished through the use of a tissue location device, described in detail below.

A tissue location device is inserted through the tissue to be repaired prior to insertion and use of the spiral suture device. As an example, an introducer is inserted into the appropriate position of the body, followed by insertion of a guidewire. Use of a guidewire is optional. The tissue location device is then inserted along the guidewire, through the tissue to be repaired.

Figure 16A:
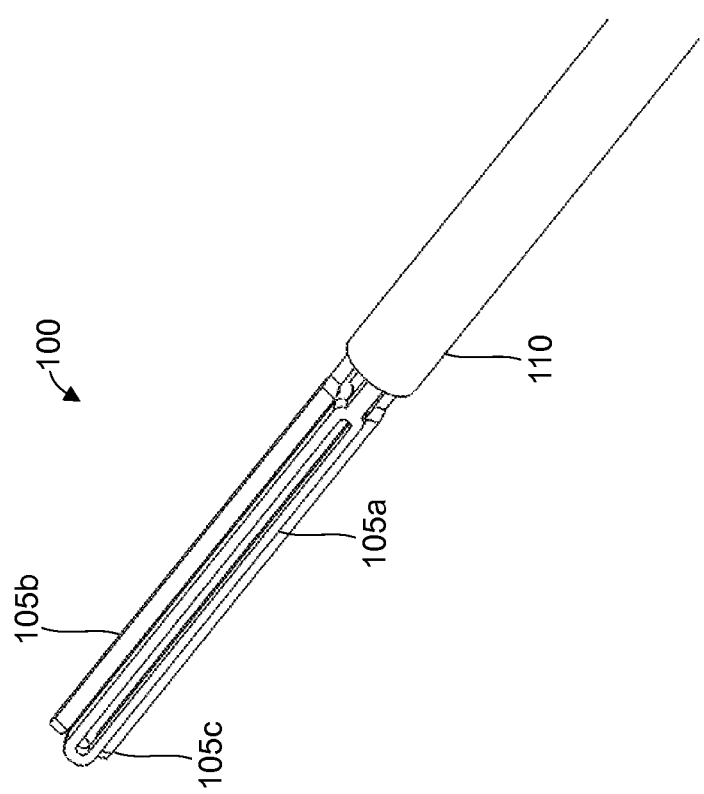
FIGS. 16A-16C illustrate embodiments of a tissue locating device.
Figure 16C:
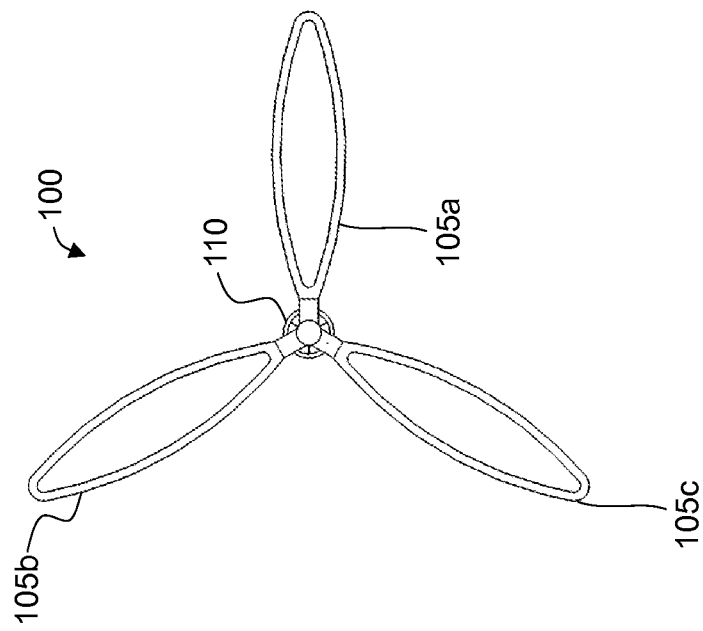
Figure 16B:
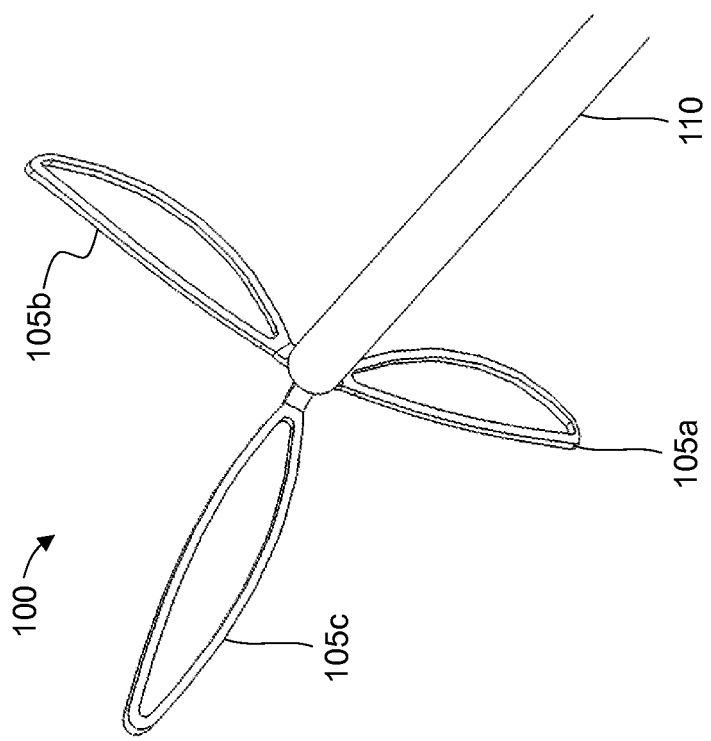

The tissue locating device is illustrated in FIGS. 16A-16C. Tissue locating device 100 has a plurality of locating members 105a,b,c which may be held in a compact position prior to delivery, folded to lie along the longitudinal axis of the tissue locating device. The plurality of locating members are held in a compact position by a locating device sheath 110 which encases plurality of locating members 105a,b,c. Locating device sheath 110 may be retracted to uncover locating members 105a,b,c, allowed the each of the locating members to expand radially as shown in FIG. 16B. FIG. 16C shows a top view of locating members 105a,b,c in an expanded condition.

It is understood that locating members of the tissue locating device can possess a wide variety of configurations which allow the members and device to function as intended. A patch of fabric or other similar material may be used to cover one or both faces of a locating member. The fabric may be bioabsorbable or biodegradable, and may be a knitted or braided fabric with a pore size and density that prohibits blood flow therethrough. In one embodiment, the fabric or covering can further include a sealing material. The sealing material can be selected from the general class of materials that include polysaccharides, proteins, and biocompatible gels. Specific examples of these polymeric materials can include, but are not limited to, those derived from poly(ethylene oxide) (PEO), poly(ethylene glycol) (PEG), poly(vinyl alcohol) (PVA), poly(vinylpyrrolidone) (PVP), poly(ethyloxazoline) (PEOX) polyaminoacids, pseudopolyamino acids, and polyethyloxazoline, as well as copolymers of these with each other or other water soluble polymers or water insoluble polymers. Examples of the polysaccharide include those derived from alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives, and carrageenan. Examples of proteins include those derived from gelatin, collagen, elastin, zein, and albumin, whether produced from natural or recombinant sources. The materials can be bioactive agents, including those that modulate thrombosis, those that encourage cellular ingrowth, throughgrowth, and endothelialization, those that resist infection, and those that reduce calcification.

Examples of suitable materials for locating members include, but are not limited to, medical grade stainless steel, elgiloy titanium, tantalum, platinum alloys, niobium alloys, cobalt alloys, gold, nickel, chromium and molybdenum, alginate, or combinations thereof. Examples of shape-memory materials include shape memory plastics, polymers, and thermoplastic materials which are inert in the body. Shape memory alloys having superelastic properties generally made from ratios of nickel and titanium, commonly known as Nitinol, are preferred materials.

Figure 17:
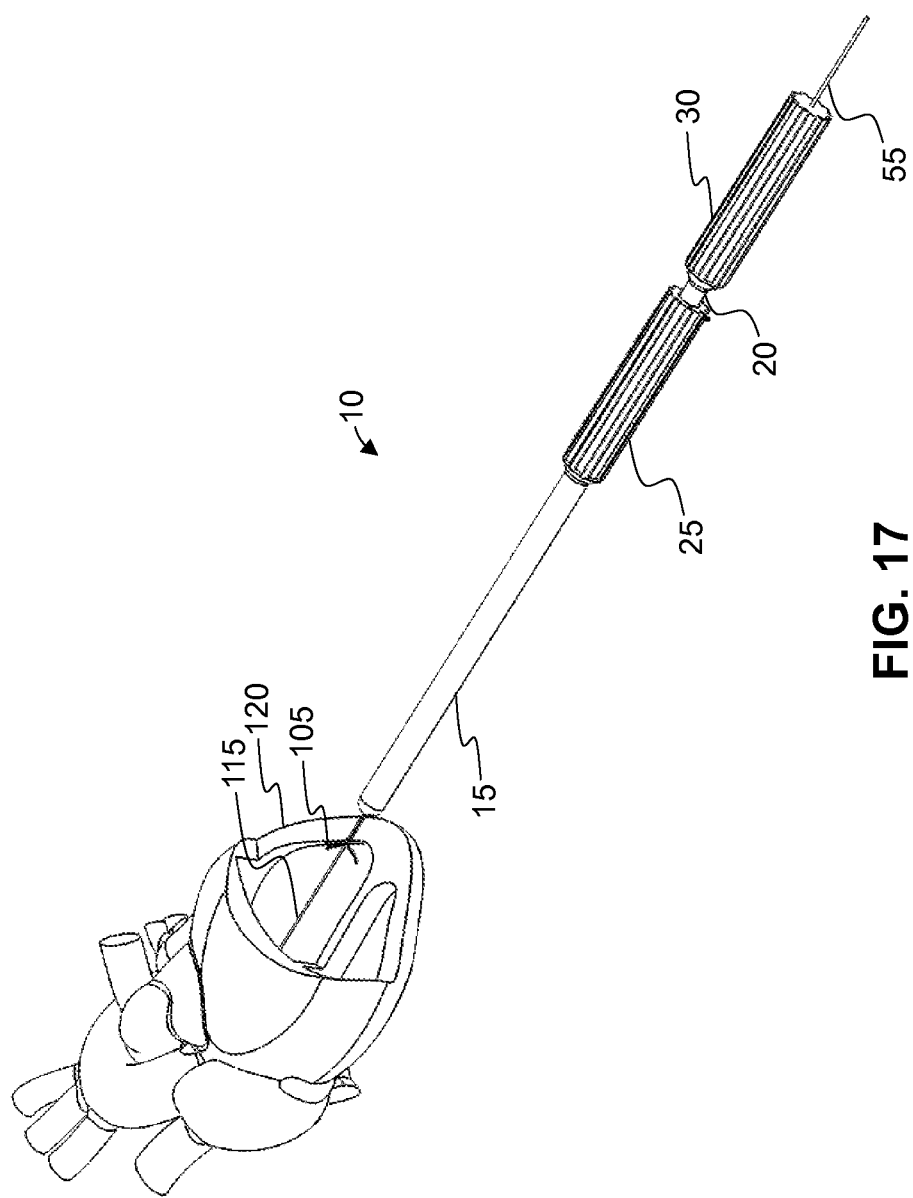
FIGS. 17-18 illustrate use of a spiral closure device.

FIG. 17 show positioning of tissue locating device 100 prior to insertion of a spiral suturing device. As seen in FIG. 17, a guidewire 115 has been inserted into the left ventricle of the heart. The distal end of tissue locating device 100 is advanced along guidewire 115 through the wall of the left ventricle (120) and into the left ventricle. The locator device sheath is pulled in a proximal direction to unsheath the locator members allowed each locator member to radially expand. Tissue locating device 100 is then pulled gently in a proximal direction until resistance is felt, indicating that locating members 105 are in contact with the internal wall of the left ventricle and thus properly position. At this time, a spiral closure device may be inserted and advanced along the tissue locating device which is thereby fed through the central sheath of the spiral closure device.

Figure 18:
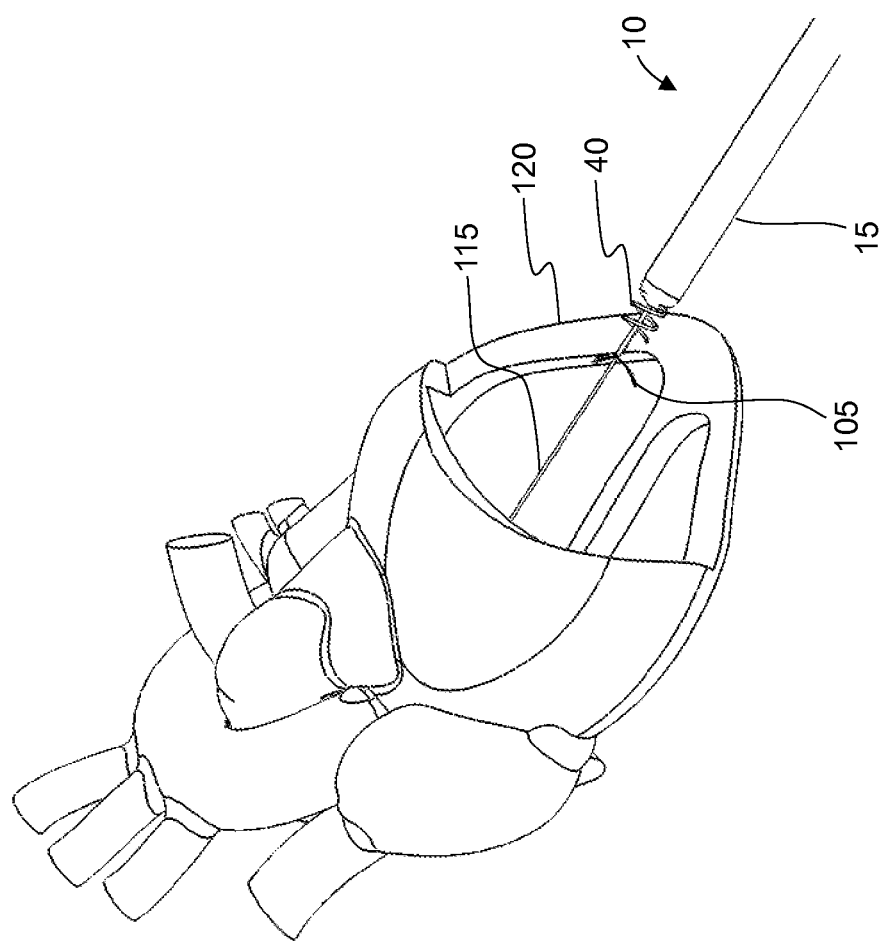

Use of a spiral closure device in concert with a tissue locating device is illustrated in part in FIG. 18. After proper positioning of the tissue locating device, spiral closure device 10 is advanced distally along the locator device sheath until the distal end of spiral closure device 10 contacts and abuts the left ventricle wall. The design of the tissue locating and spiral closure devices is such that the user knows the length of each. In addition, the thickness of the ventricle wall is approximately known by the practitioner. Accordingly, by placing positioning marks on the proximal end of the locating device sheath, one may use this mark to monitor how are to advance the spiral needle to capture the correct amount of tissue. Using such marks, the inner sheath handle is rotated to advance the spiral needle distally out of the distal end of outer sheath 15 and through the tissue along a helical path around the opening to be repaired. The inner sheath handle is rotated along the outer sheath for an appropriate distance to ensure the spiral needle has advanced through the desired depth of tissue. The spiral needle is then retracted along the same helical path by an opposite rotation of the inner sheath handle, leaving the suture threaded through the tissue, optionally secured by multiple barbs as described above. Finally, the spiral closure device is completely removed from the patient, leaving behind only a length of suture both threaded through the tissue in a helical pattern and extending from the external surface of the tissue.

The excess length extending from the external surface of the tissue is used to control tension in the suture threaded through the tissue. For example, the locating device sheath can be pushed in a distal direction while pulling the suture gently in a proximal direction to localize tension near the external surface of the tissue.

The tissue locating device can be retracted and removed from the patient by first pushing locating device sheath 110 distally to encase and compact the locating members, followed by pulling tissue locating device 100 in a proximal direction along the guidewire until the device is removed from the patient. At this time, only the suture and guidewire remain.

Importantly, immediately after threading of the suture through the tissue surrounding the opening which is to eventually be repaired and closed, the opening still exists. Thus, other devices such as valvuplasty balloons and valve replacements can be advanced along the guidewire, passing through the opening which is surrounded by the suture helix. It is only after the desired procedure is completed and devices removed that the suture is pulled to close the opening. The barbs of the suture ensure the opening that was in the tissue remains closed.

After removal of the device, the suture is tightened. For example, when tension is placed on the distal end of the suture, the suture is drawn down to tighten the access opening, but the barbs prevent the access point from opening.

Figure 19A:
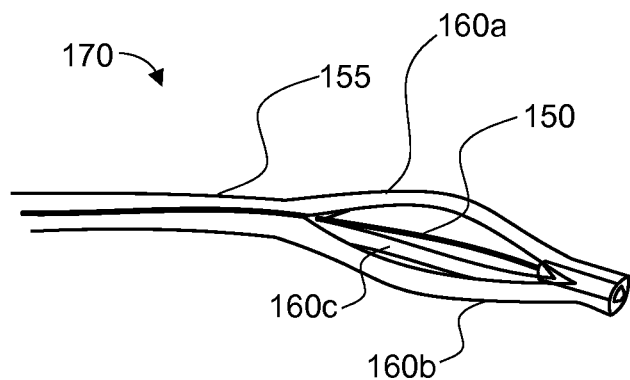
FIGS. 19A-19C illustrate a tissue locating device comprising a split tube.
Figure 19B:
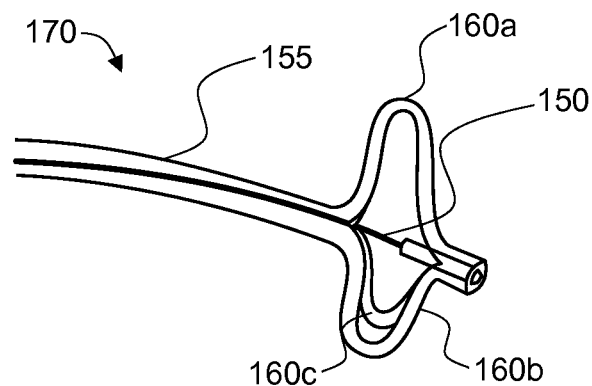
Figure 19C:
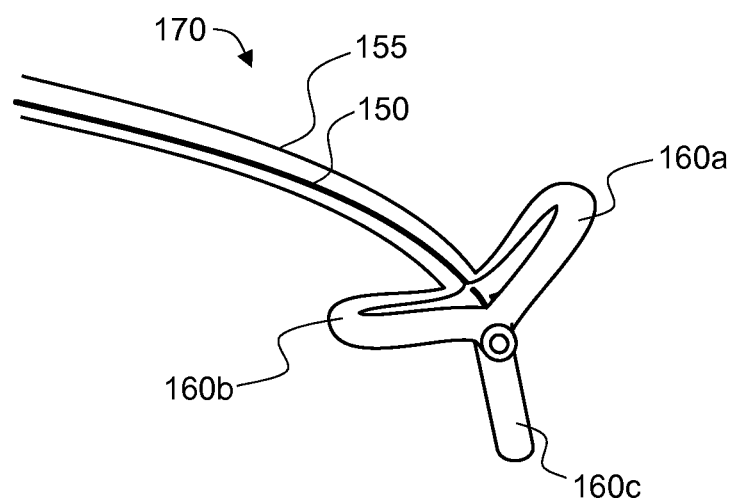

An alternative tissue locating device comprising a split tube is illustrated in FIGS. 19A-19C, and referred to herein as a split tube locating device 170. In this embodiment, a wire 150 or similar structure is encased in a flexible tubing 155. Flexible tubing 155 can be made of a polymer, plastic, rubber, or similar material. The distal end of wire 150 is fixed or otherwise attached to the distal end of tubing 155. Near the distal end of wire 150, one or more longitudinal slits are created in tubing 155 near the distal end of tubing 155 to form one or more tubing contact members, e.g., 160a,b,c. The distal end of split tube locating device 170 can be inserted through a tissue opening or access point at least until the full lengths of the one or more tube contact members are completely through the tissue opening. At this time, wire 150 can be retracted or pulled in a proximal direction such that each of tube contact members 160a,b,c, become compressed to form a radially expanded structure as shown in FIGS. 19B-19C. In one embodiment, a fabric or similar material may be attached to the one or more tube contact members wherein the fabric and tubing contact members 160 form an umbrella-like structure, and wherein the fabric facilitates the sealing of the tissue opening.

Figure 20B:
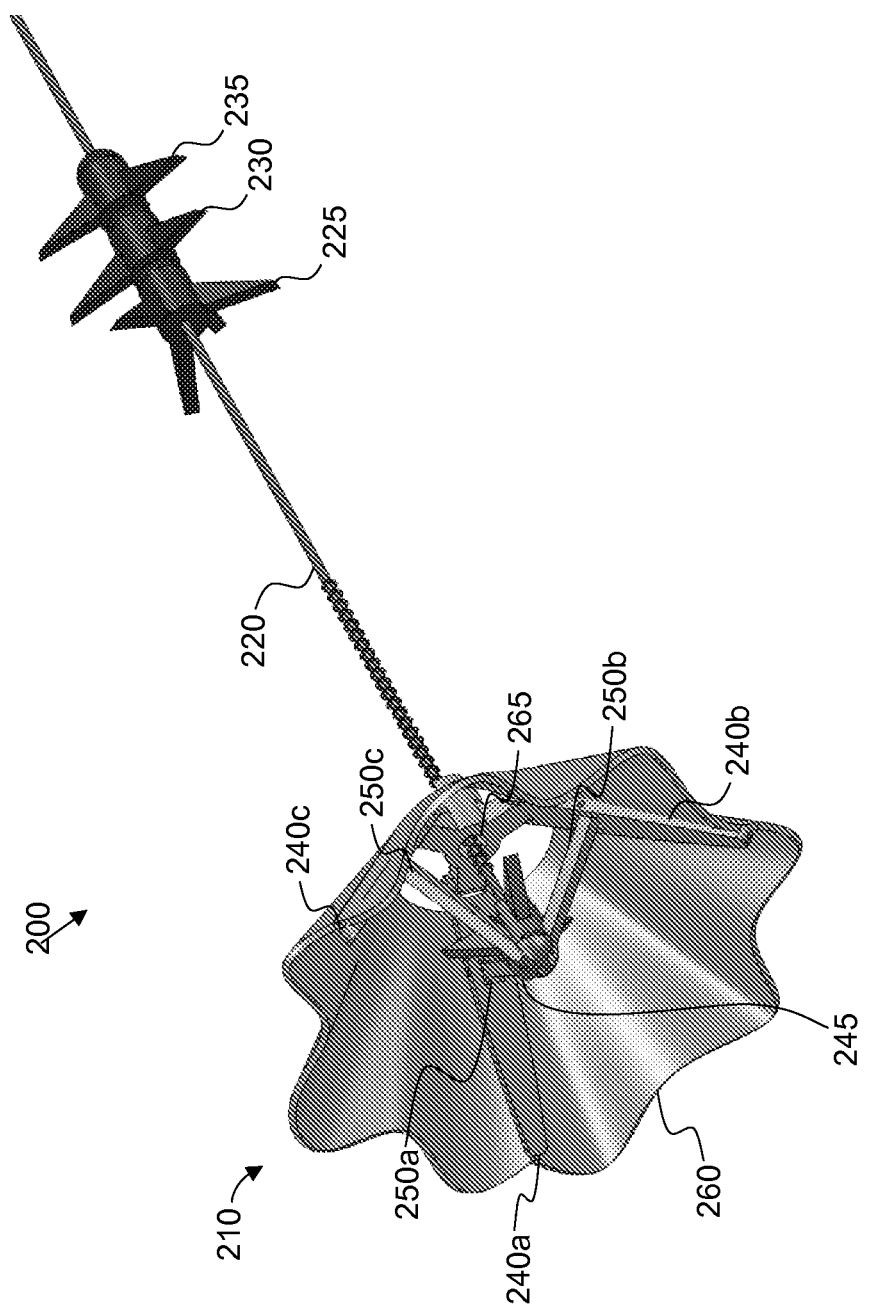

A second embodiment for a tissue locating device is provided herein and illustrated in FIGS. 20A-20B as 200. Tissue locating device 200 comprises a threaded central member 220 attached via screw threads at its distal end to a tissue engager 210. Near the proximal end of threaded central member 220 are a first rotational control 225, a second rotational control 230 and a third rotational control 235.

Collapsible tissue engager 210, as shown in FIG. 20B, comprises three adjustable arms 240a,b,c, three arm connectors 250a,b,c (250c is not visible in FIG. 20B), a central connector 245, and an optional fabric piece 260. By rotating first rotational control 225, threaded central member 220 moves proximally through the center aperture 265 of tissue engager 210, pulling on central connector 245, and resulting in radial extension of arm connectors 250a,b,c, and adjustable arms 240a,b,c. If a fabric piece, e.g., fabric piece 260 is present, is become fully expanded and flat. Tissue locator 200 may then be pulled proximally until tissue engager 210 abuts or otherwise contacts the internal surface of the tissue wall. Rotation of second rotational control 230 functions to disconnect threaded central member 220 from tissue engager 210.

It is understood by the skilled artisan that other elements may be used in a tissue locating device, wherein the element is able to pass through the opening to be closed in a compact state, then expanded once the element is completely through the tissue opening. For example, a balloon structure such as an angioplasty balloon could be used.

Vascular Closure Device

Transfemoral percutaneous coronary procedures have become a mainstay in both diagnostic and interventional cardiology over the past several years. However, safe management of vascular access sites after removal of percutaneous catheters remains a serious concern and challenge. One traditional method for closure of the femoral artery is manual compression of the site. This method is associated with a complication rate of up to 5% as well as significant discomfort and immobility for patients, sometimes requiring prolonged hospitalization.

Recent developments of vascular closure devices have resulted in FDA approved devices which replace manual compression and are associated with decreased length of hospital stay and increased patient comfort. Examples of such devices include an implantable collagen plug (VasoSeal, Datascope corp. Montvale, N.J.) and a percutaneous suture device (Perclose, Percose, Inc. Redwood City, Calif.). Compared with traditional methods used to achieve hemostasis, these closure devices have high overall levels of safety and efficacy. Major complications such as vascular repair surgery, bleeding requiring transfusion, and infection associated with the collagen plug are 2.9%, and the incidence of minor complications, including hematoma, bleeding, and pseudoaneurysm, is 7.2% or less. Complications associated with the percutaneous suture device are 11%. Despite these encouraging statistics, there remains a need to improve vascular closure technologies to make it easier, more reliable and more cost-effective.

Disclosed herein is a vascular closure device which provides easy access to the opening in the vascular wall and a reliable method for stemming blood flow out of the access point until the vascular wall has fully closed.

Figure 21B:
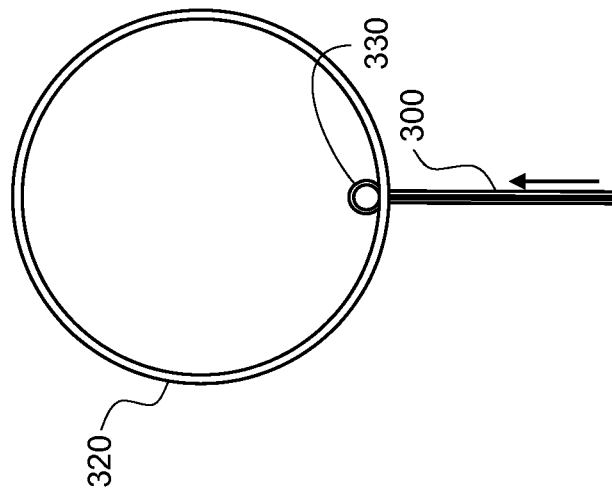
FIGS. 21A-21B illustrate a vascular closure device.
Figure 21A:
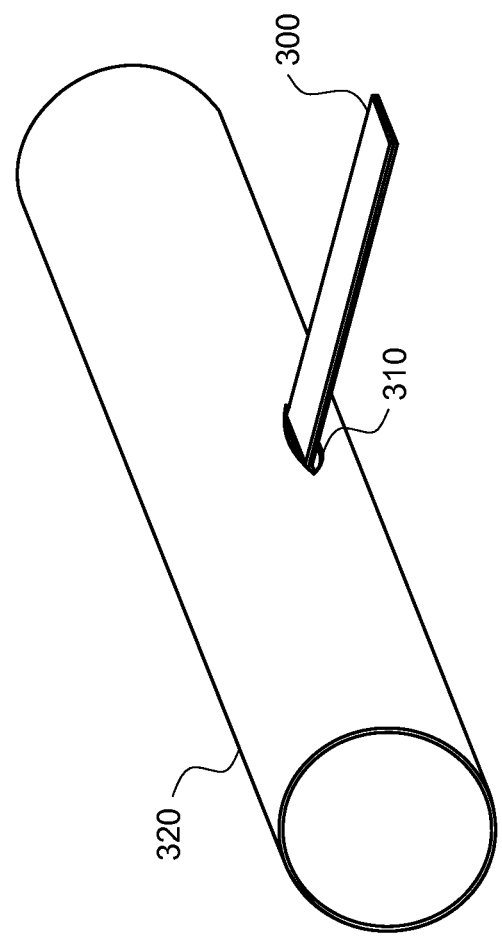

FIG. 21A shows a vessel 320 with an access point 310 formed, for example, during a percutaneous procedure. The shape of a thin sheet 300 is folded onto itself such that a loop structure 330 is formed at the point of folding. It is understood that the dimensions of sheet 300 can vary depending on the immediate need. For example, the width of the sheet should be less than the greatest width of the access point. The sheet may be formed from any number of biocompatible materials including, but not limited to a fabric comprised of, for example, a material identified by a trade name selected from Nylon®, Dacron®, or Teflon®, or is expanded polytetrafluoroethylene (ePTFE), and/or other materials. Preferably, the sheet would be made from a bioabsorbable material. A simple device could be used to maintain sheet 300 in a desired configuration such as that shown in FIG. 21B, and to deliver the sheet to the site through the percutaneous puncture site, via, for example, an introducer.

Once loop structure 330 is within the vessel lumen as shown in FIG. 21C, further advancing of sheet 300 into the vessel lumen will result in increasing the diameter of loop structure 300 within the vessel lumen. Sheet 300 and loop structure 330 are pushed further into the vessel lumen until loop structure 330 is in full contact with the internal wall of the vessel lumen, thus fully lining the circumference of the vessel lumen.

In one embodiment, the device used to delivery sheet 300 also functions to remove any excess of sheet 300. Removal of the excess may occur by any number of means readily appreciated by skilled artisans.

A number of embodiments of the present invention will below be described with reference to the attached drawings. It should be understood that the various elements of any one particular embodiment may be utilized in one or more of the other embodiments, and thus combinations thereof are within the scope of the appended claims.

The invention claimed is:

1. A vascular closure assembly comprising:
a sealing tube, wherein said sealing tube comprises a proximal end portion and a distal end portion;
a sheath which encases at least a portion of the sealing tube in a folded configuration;
a tubing member positioned within the sealing tube, wherein the tubing member comprises proximal and distal sections, the distal section of the tubing member having longitudinal slits extending therealong to form a plurality of force application elements from a plurality of tubing contact members, the force application elements being movable from a radially collapsed configuration to a radially expanded configuration for expanding the distal end portion of the sealing tube from the folded configuration; and
a wire positioned within the tubing member and comprising a distal end fixed to the tubing member distal section, the wire being retractable relative to the tubing member proximal section to radially expand the force application elements and the sealing tube, wherein the distal end portion of the sealing tube is configured to radially flare out for flattening against surrounding tissue at a surgical access site upon actuation of the force application elements.

2. The closure assembly of claim 1, wherein the sealing tube comprises pericardial tissue.

3. The vascular closure assembly of claim 1, wherein the plurality of tubing contact members comprises three tubing contact members.

4. The vascular closure assembly of claim 1, wherein the tubing member comprises three of said longitudinal slits.

5. The vascular closure assembly of claim 4, wherein the longitudinal slits extend parallel relative to a longitudinal axis of the tubing member.

6. The vascular closure assembly of claim 1, wherein distal advancement of the wire permits the tubing contact members to move to the radially collapsed configuration.

7. The vascular closure assembly of claim 1, wherein the sheath is proximally retractable relative to the tubing member to permit expansion of the tubing member distal section.

8. The vascular closure assembly of claim 1, wherein upon expansion and contraction of the tubing member distal section, the tubing member is proximally retractable from within the sealing tube.

9. The vascular closure assembly of claim 1, wherein the proximal end portion of the sealing tube is open.

10. The vascular closure assembly of claim 1, wherein the distal end portion of the sealing tube is closed.

11. The vascular closure assembly of claim 1, wherein the distal end portion of the sealing tube includes a guidewire aperture.

12. The vascular closure assembly of claim 11, wherein the distal end portion of the sealing tube flares out and converges at the guidewire aperature formed in the distal end portion.

13. A vascular closure assembly comprising:
a sealing tube having an open end, a closed end, and a lumen extending therebetween; and
a tubing member positioned within the sealing tube lumen, the tubing member having proximal and distal sections and a split-tube expansion mechanism at the distal section, the split-tube expansion mechanism comprising a wire coupled to the tubing member distal section and a plurality of force application elements formed from a plurality of tubing contact members that are expandable from a radially collapsed configuration to cause radial flaring of the sealing tube closed end from a folded configuration for contacting the sealing tube closed end against surrounding tissue at a surgical access site upon actuation of the wire.

14. The vascular closure assembly of claim 13, wherein the closed end of the sealing tube includes a guidewire aperture.

15. The vascular closure assembly of claim 13, further comprising a sheath, the sealing tube and the tubing member being positioned within the sheath to facilitate delivery of the assembly to an access site for a surgical procedure, wherein the sheath is proximally retractable relative to the tubing member to permit expansion of the tubing member distal section.

16. The vascular closure assembly of claim 13, wherein the plurality of tubing contact members comprises three tubing contact members.

17. The vascular closure assembly of claim 13, wherein the split-tube expansion mechanism comprises three longitudinal slits extending along the tubing member.

18. The vascular closure assembly of claim 17, wherein the longitudinal slits extend parallel relative to a longitudinal axis of the tubing member.

19. The vascular closure assembly of claim 13, wherein distal advancement of the wire permits the tubing contact members to move to the radially collapsed configuration.

20. A vascular closure assembly comprising:
a sealing tube having proximal and distal end portions and a lumen extending therebetween; and
a tubing member positioned within the sealing tube lumen, the tubing member having proximal and distal sections and a split-tube expansion mechanism at the distal section, the split-tube expansion mechanism comprising a wire coupled to the tubing member distal section and a plurality of force application elements formed from a plurality of tubing contact members, the plurality of force application elements being radially expandable, upon actuation of the wire, for urging the sealing tube distal end portion radially outwardly from a folded configuration to permit sealing of the distal end portion against surrounding tissue at a surgical access site.

21. The vascular closure assembly of claim 20, wherein the distal end portion of the sealing tube is closed.

22. The vascular closure assembly of claim 20, wherein the distal end portion of the sealing tube includes a guidewire aperture.

* * * * *